United States Patent
Heckel et al.

(10) Patent No.: US 9,126,982 B2
(45) Date of Patent: Sep. 8, 2015

(54) HETEROCYCLIC COMPOUNDS, MEDICAMENTS CONTAINING THEM, USE AND PROCESSES FOR THE PREPARATION THEREOF

(71) Applicants: Armin Heckel, Biberach an der Riss (DE); Joerg Kley, Mittelbiberach (DE)

(72) Inventors: Armin Heckel, Biberach an der Riss (DE); Joerg Kley, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/322,940

(22) Filed: Jul. 3, 2014

(65) Prior Publication Data

US 2015/0011535 A1  Jan. 8, 2015

(30) Foreign Application Priority Data

Jul. 8, 2013 (EP) .................................. 13175552

(51) Int. Cl.

| | |
|---|---|
| *A61K 31/4965* | (2006.01) |
| *A61K 31/497* | (2006.01) |
| *C07D 241/20* | (2006.01) |
| *C07D 401/12* | (2006.01) |
| *C07D 401/14* | (2006.01) |
| *C07D 403/12* | (2006.01) |
| *C07D 403/14* | (2006.01) |
| *C07D 413/12* | (2006.01) |
| *C07D 417/12* | (2006.01) |
| *A61K 31/541* | (2006.01) |
| *A61K 31/5377* | (2006.01) |
| *A61K 31/551* | (2006.01) |
| *A61K 45/06* | (2006.01) |
| *C07D 241/28* | (2006.01) |

(52) U.S. Cl.
CPC ............ *C07D 403/12* (2013.01); *A61K 31/497* (2013.01); *A61K 31/4965* (2013.01); *A61K 31/5377* (2013.01); *A61K 31/541* (2013.01); *A61K 31/551* (2013.01); *A61K 45/06* (2013.01); *C07D 241/20* (2013.01); *C07D 241/28* (2013.01); *C07D 401/12* (2013.01); *C07D 401/14* (2013.01); *C07D 417/12* (2013.01)

(58) Field of Classification Search
CPC .. C07D 241/20; C07D 401/12; C07D 401/14; C07D 403/12; C07D 403/14; C07D 413/12; C07D 417/12
See application file for complete search history.

(56) References Cited

FOREIGN PATENT DOCUMENTS

| WO | 2007071396 A2 | 6/2007 |
| WO | 2013064450 | 5/2013 |
| WO | 2013092674 A1 | 6/2013 |

OTHER PUBLICATIONS

Hirsh, et al., Journal of Medicinal Chemistry, American Chemical Society, vol. 49, No. 14, 2006, p. 4098-4115.
Rogister, et al., European Journal of Medicinal Chemistry, Editions Scientifique Elsevier, Paris, "Novel Inhibitors of the Sodium-Calcium Exchanger: Benzene Ringer Analogues of N-Guanidino Substituted Amiloride Derivatives" vol. 36, No. 7-8, 2001, p. 597-614.
Russ, et al., Archiv der Pharmazie, Wiley Verlag, Weinheim, "Preparation and Diuretic Properties of Novel Amiloride Analogues", vol. 325, No. 12, 1992, p. 761-767.

*Primary Examiner* — Brian McDowell
(74) *Attorney, Agent, or Firm* — Michael P. Morris; Edward S. Laser

(57) ABSTRACT

The present invention relates to compounds of general formula (I)

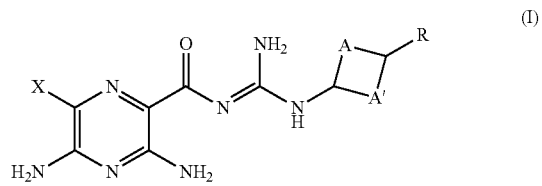

and the tautomers and the salts thereof, particularly the pharmaceutically acceptable salts thereof with inorganic or organic acids and bases, which have valuable pharmacological properties, particularly an inhibitory effect on epithelial sodium channels, and the use thereof for the treatment of diseases, particularly diseases of the lungs and airways.

10 Claims, No Drawings

HETEROCYCLIC COMPOUNDS, MEDICAMENTS CONTAINING THEM, USE AND PROCESSES FOR THE PREPARATION THEREOF

FIELD OF THE INVENTION

The present invention relates to compounds of general formula (I)

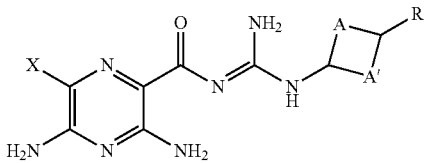

and the tautomers and the salts thereof, particularly the pharmaceutically acceptable salts thereof with inorganic or organic acids and bases, which have valuable pharmacological properties, particularly an inhibitory effect on epithelial sodium channels, the use thereof for the treatment of diseases, particularly diseases of the lungs and airways.

BACKGROUND INFORMATION

Amiloride type compounds are known from the prior art as active substances for example for the treatment of diseases of the lungs and airways (J. Med. Chem. 49 (2006) 4098-4115). WO 08135557 discloses compounds of similar structure showing ENaC (Epithelial Sodium Channel) inhibitor activity.

The problem of the present invention is to prepare new compounds which may be used therapeutically for the treatment of pathophysiological processes treatable by the blockade of an epithelial sodium channel, particularly for the treatment of the lungs and airways.

BRIEF SUMMARY OF THE INVENTION

It has surprisingly been found that the problem mentioned above is solved by compounds of formula (I) of the present invention. The new compounds of the present invention exhibit a reduced permeability being beneficial for topical lung treatment.

DETAILED DESCRIPTION OF THE INVENTION

The present invention relates to a compound of formula (I),

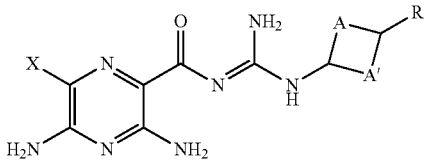

wherein
A, A' denote independently from each other —$CH_2$— or —$CH_2$—$CH_2$—;
R is —$NR^1R^2$, —$NR^3R^4R^{5(+)}Z_1^{(-)}$ or $OR^{13}$;
X is halogen, preferably Cl or Br;
$Z_1^{(-)}$ is halogen anion or an organic acid anion,
$Z_2^{(-)}$ is halogen anion or an organic acid anion,
$Z_3^{(-)}$ is halogen anion or an organic acid anion,
$Z_4^{(-)}$ is halogen anion or an organic acid anion,
$R^1$, $R^2$ are selected independently from each other
H, —$C(NH_2)NH$, —$CN(CH_3)_2N(CH_3)_2^+Z_2^-$, —$C_{1-3}$-alkyl, —$C_{2-4}$-alkyl-$N(CH_3)_2$, —$C_{1-3}$-alkyl-phenyl-$R^{12}$, —$C_{1-3}$-alkyl-COOH, —$C_{1-4}$-alkyl-CO—$Y^2$—$R^{11}$, —CO-phenyl-CO—O—$R^{13}$, —CO—$C_{1-4}$-alkyl, —CO—$C_{1-3}$-alkyl-$NR^6R^7$, —CO—$C_{1-3}$-alkyl-$N(CH_3)_3^+Z_3^-$, —CO—$C_{1-4}$-alkyl-$Y^1$—$R^9$, —CO—O—$C_{1-4}$-alkyl-$R^8$, —CO—NH—$C_{3-7}$-cycloalkyl, —CO—NH—$C_{1-4}$-alkyl, —$CH_2$—CO—O—$C_{1-3}$-alkyl, —$CH_2$—CO—O—$C_{1-3}$-alkyl-phenyl and —$SO_2$—$R^{10}$;
$R^6$ is selected from among -$C_{1-3}$-alkyl, H, —$C_{1-4}$-alkyl-OH, —$CH_2$—CO—O—$C_{1-3}$-alkyl and —$CH_2COOH$;
$R^7$ is selected from among -$C_{1-3}$-alkyl, —CO—O—$C_{1-3}$-alkyl, —$C_{1-4}$-alkyl-OH, H, —$CH_2$—CO—O—$C_{1-3}$-alkyl and —$CH_2COOH$;
$R^8$ is H or phenyl;
$R^9$ is selected from among H, —$C_{1-3}$-alkyl, OH, —$NR^6R^7$ and =O;
$R^{10}$ is $C_{1-3}$-alkyl or an optionally substituted N-containing nonaromatic heterocycle;
$R^{11}$ is selected from among H, $C_{1-3}$-alkyl, =O, —$N(CH_3)_2$ and —$N(CH_3)_3^+Z_4^-$;
$R^{12}$ is selected from among H, halogen, —COOH, —PO($OC_{1-4}$-alkyl)OH, optionally substituted at the 2, 3 or 4 position of the $C_{1-4}$-alkyl group by —$N(C_{1-3}$-alkyl$)_2$ or —$N(C_{1-3}$-alkyl$)_3^+Z_4^-$, and —PO($OC_{1-4}$-alkyl$)_2$, —PO$(OH)_2$;
$R^{13}$ is H or $C_{1-4}$-alkyl;
$Y^1$ is selected from among an optionally substituted 5- to 8-membered N-containing nonaromatic heterocycle, —$N(C_{1-3}$-alkyl$)$-$C_{2-4}$-alkyl-$N(C_{1-3}$-alkyl$)_2$ and —$N(C_{1-3}$-alkyl$)$-$C_{2-4}$-alkyl-$N^+(C_{1-3}$alkyl$)_3Z_1^{(-)}$;
$Y^2$ is an optionally substituted 5- to 8-membered N-containing nonaromatic heterocycle;
or $R^1$ and $R^2$ are together with the nitrogen atom they are attached to an optionally substituted 4-7-membered heterocycle, containing at least one N and optionally one or more heteroatoms selected from the group consisting of piperazino, morpholino, piperidino; thiomorpholino, thiomorpholino-1-oxide, thiomorpholinon-1,1-dioxide, diazepane and pyrrolidino, wherein the nitrogen atoms may be substituted by a group selected from among phenyl, $C_{1-3}$-alkylsulfonyl, $C_{1-3}$-alkyl and —CO—$C_{1-3}$-alkyl;
$R^3$, $R^4$, $R^5$ denote independently from each other —$C_{1-3}$-alkyl;
or tautomers or pharmacologically acceptable acid addition salts thereof.

Preferred compounds of formula (I) are those, wherein
A, A' are both —$CH_2$—$CH_2$—;
R is —$NR^1R^2$ or —$NR^3R^4,R^{5(+)}X^{(-)}$;
X is halogen;
$R^1$, $R^2$ are selected independently from each other from
H, —$C(NH_2)NH$, —$CN(CH_3)_2N(CH_3)_2^+Z_2^-$, —$C_{1-3}$-alkyl, —$C_{2-4}$-alkyl-$N(CH_3)_2$, —$C_{1-3}$-alkyl-phenyl-$R^{12}$, —$C_{1-3}$-alkyl-COOH, —$C_{1-4}$-alkyl-CO—$Y^2$—$R^{11}$, —CO-phenyl-CO—O—$C_{1-4}$—$R^{13}$, —CO—$C_{1-4}$-alkyl, —CO—$C_{1-3}$-alkyl-$NR^6R^7$, —CO—$C_{1-3}$-alkyl-$N(CH_3)_3^+Z_3^-$, —CO—$C_{1-4}$-alkyl-$Y^1$—$R^9$, —CO—O—$C_{1-4}$-alkyl-$R^8$, —CO—NH—$C_{3-7}$-cycloalkyl, —CO—NH—$C_{1-4}$-alkyl, —CH$_2$—CO—O—C$_{1-3}$-alkyl, —CH$_2$—CO—O—C$_{1-3}$-alkyl-phenyl, and —SO$_2$—R$^{10}$;

R$^6$ is selected from —C$_{1-3}$-alkyl, H, —C$_{1-4}$-alkyl-OH, —CH$_2$—CO—O—C$_{1-3}$-alkyl and —CH$_2$COOH;

R$^7$ is selected from among-C$_{1-3}$-alkyl, —CO—O—C$_{1-3}$-alkyl, —C$_{1-4}$-alkyl-OH, H, —CH$_2$—CO—O—C$_{1-3}$-alkyl and —CH$_2$COOH;

R$^8$ is H or phenyl;

R$^9$ is selected from among H, —C$_{1-3}$-alkyl, —OH, —NR$^6$R$^7$ and =O;

R$^{10}$ is C$_{1-3}$-alkyl or an optionally substituted N-containing nonaromatic heterocycle;

R$^{11}$ is selected from among H, —C$_{1-3}$-alkyl, =O, —N(CH$_3$)$_2$ and —N(CH$_3$)$_3$$^+$X$^-$;

R$^{12}$ is H or halogen;

R$^{13}$ is H or —C$_{1-4}$-alkyl;

Y$^1$ is an optionally substituted 5- to 8-membered N-containing nonaromatic heterocycle;

Y$^2$ is an optionally substituted 5- to 8-membered N-containing nonaromatic heterocycle;

or R$^1$ and R$^2$ are together with the nitrogen atom they are attached to an optionally substituted 4-7-membered heterocycle containing at least one N-atom;

R$^3$, R$^4$, R$^5$ denote independently from each other —C$_{1-3}$-alkyl;

or tautomers or pharmacologically acceptable acid addition salts thereof.

Also preferred are compounds of formula (I), wherein R is —NR$^1$R$^2$;

or tautomers or pharmacologically acceptable acid addition salts thereof.

Also preferred are compounds of formula (I), wherein R$^1$, R$^2$ denote independently from each other —C$_{1-4}$-alkyl-CO—Y$^2$—R$^{11}$ or —CO—C$_{1-4}$-alkyl-Y$^1$—R$^9$;

R$^9$ is selected from among H, —C$_{1-3}$-alkyl, —OH, —NR$^6$R$^7$ and =O;

R$^{11}$ is selected from among H, —C$_{1-3}$-alkyl, =O, —N(CH$_3$)$_2$ and —N(CH$_3$)$_3$$^+$X$^-$;

Y$^1$ is selected from a linker of formula (a1) to (j1)

(a1)

(b1)
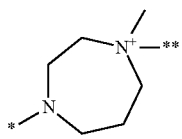

(c1)
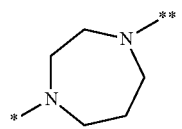

(d1)
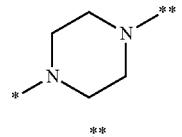

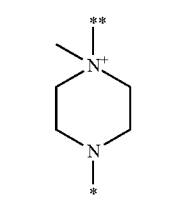

-continued (e1)
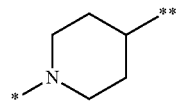

(f1)
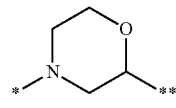

(g1)
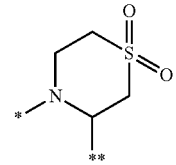

(h1)
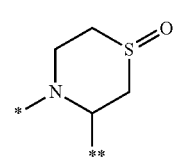

(i1)
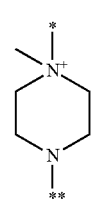

(j1)
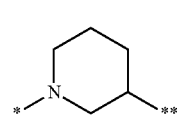

wherein

* denotes the attachment point to the alkyl moiety of —CO—C$_{1-4}$-alkyl-*

** denotes the attachment point to R$^9$

Y$^2$ is selected from a linker of formula (a2) to (h2)

(a2)
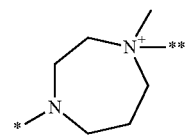

(b2)
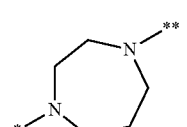

(c2)
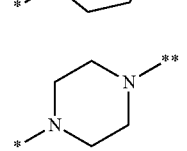

-continued

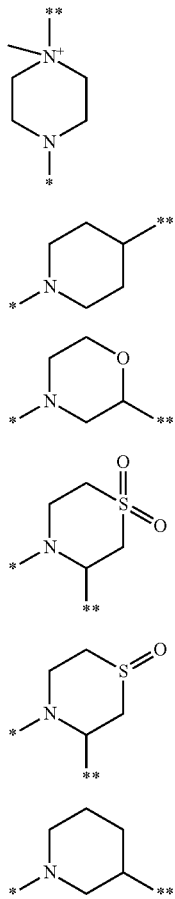

wherein
* denotes the attachment point to the carbonyl moiety of —C$_{1-4}$-alkyl-CO—*
** denotes the attachment point to R$^{11}$ or tautomers or pharmacologically acceptable acid addition salts thereof.

Also preferred are compounds of formula (I), wherein R$^1$, R$^2$ independently from each other denote —C(NH$_2$)NH or —CN(CH$_3$)$_2$N(CH$_3$)$_2^+$Z$_2^-$;
or tautomers or pharmacologically acceptable acid addition salts thereof.

Also preferred are compounds of formula (I), wherein R$^1$, R$^2$ independently from each other are selected from among
H, —C$_{1-3}$-alkyl, —C$_{2-4}$-alkyl-N(CH$_3$)$_2$, —C$_{1-3}$-alkyl-phenyl-R$^{12}$, —C$_{1-3}$-alkyl-COOH, —CH$_2$—CO—O—C$_{1-3}$-alkyl and —CH$_2$—CO—O—C$_{1-3}$-alkyl-phenyl;
or tautomers or pharmacologically acceptable acid addition salts thereof.

Particularly preferred are compounds of formula (I), wherein
R$^1$, R$^2$ independently from each other are selected from among —CO-phenyl-CO—O—C$_{1-4}$—R$^{13}$, —CO—C$_{1-4}$-alkyl and —CO—C$_{1-3}$-alkyl-NR$^6$R$^7$;
or tautomers or pharmacologically acceptable acid addition salts thereof.

Also particularly preferred are compounds of formula (I), wherein
R$^1$, R$^2$ independently from each other denote —CO—O—C$_{1-4}$-alkyl-R$^8$ or —SO$_2$—R$^{10}$;

or tautomers or pharmacologically acceptable acid addition salts thereof.

Also particularly preferred are compounds of formula (I), wherein
R$^1$ or R$^2$ is hydrogen;
or tautomers or pharmacologically acceptable acid addition salts thereof.

A further embodiment of the current invention is compounds of formula (I) or a pharmaceutically acceptable salt thereof for use as a medicament.

A further embodiment of the current invention is compounds of formula (I) or a pharmaceutically acceptable salt thereof for use in the treatment of a disease selected from among respiratory diseases or complaints and allergic diseases of the airways.

A further embodiment of the current invention is compounds of formula (I) or a pharmaceutically acceptable salt thereof for use in the treatment of a disease selected from among chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), pediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema and pneumonitis of different origins.

A further embodiment of the current invention is a pharmaceutical composition comprising at least one compound of formula (I) or a pharmaceutically acceptable salt thereof and a pharmaceutically acceptable carrier.

A further embodiment of the current invention is medicament combinations which contain, besides one or more compounds of a compound of formula (I), as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators or double or triple combinations thereof.

TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, C$_{1-6}$-alkyl means an alkyl group or radical having 1 to 6 carbon atoms. In general, for groups comprising two or more subgroups, the last or first named subgroup is the radical attachment point indicated as open hyphen, for example, the substituent "aryl-C$_{1-3}$-alkyl-" means an aryl group which is bound to a C$_{1-3}$-alkyl-group, the latter of which is bound to the core or to the group to which the substituent is attached.

If a compound of the present invention is depicted in the form of a chemical name and also as a formula, in case of any discrepancy the formula shall prevail.

An asterisk is may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, trifluoroacetates, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Unless specifically indicated, according to the invention a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

The term halogen generally denotes fluorine, chlorine, bromine and iodine.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "carbocyclyl" as used either alone or in combination with another radical, means a mono- or multi-ring ring structure consisting only of carbon containing between one and four rings wherein such rings may be attached together in a pendent manner or may be fused. The term "carbocycle" refers to fully saturated and aromatic ring systems and partially saturated ring systems. The term "carbocycle" additionally encompasses spiro systems, and bridged systems.

The term "$C_{3-n}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

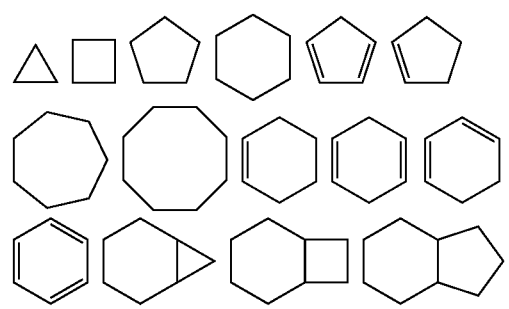

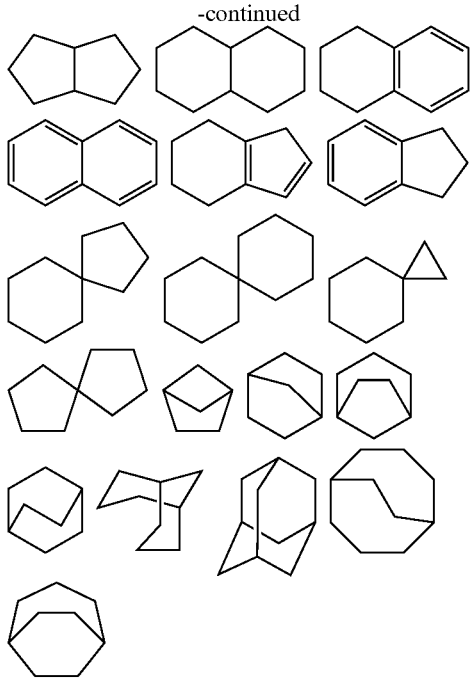

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" means a saturated or unsaturated mono- or polycyclic-ring systems including aromatic ring system containing one or more heteroatoms selected from N, O or S(O), with r=0, 1 or 2 wherein none of the heteroatoms is part of the aromatic ring. The term "heterocycle" is intended to include all the possible isomeric forms.

Thus, the term "heterocyclyl" includes the following exemplary structures which are not depicted as radicals as each form may be attached through a covalent bond to any atom so long as appropriate valences are maintained:

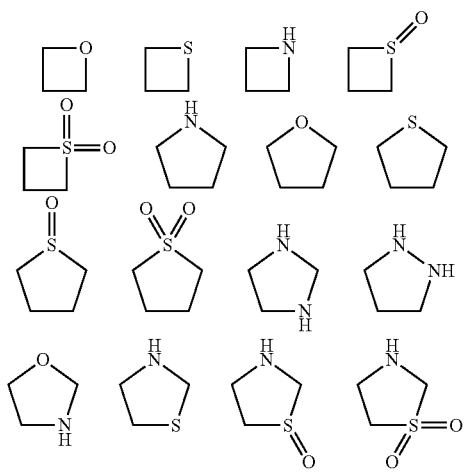

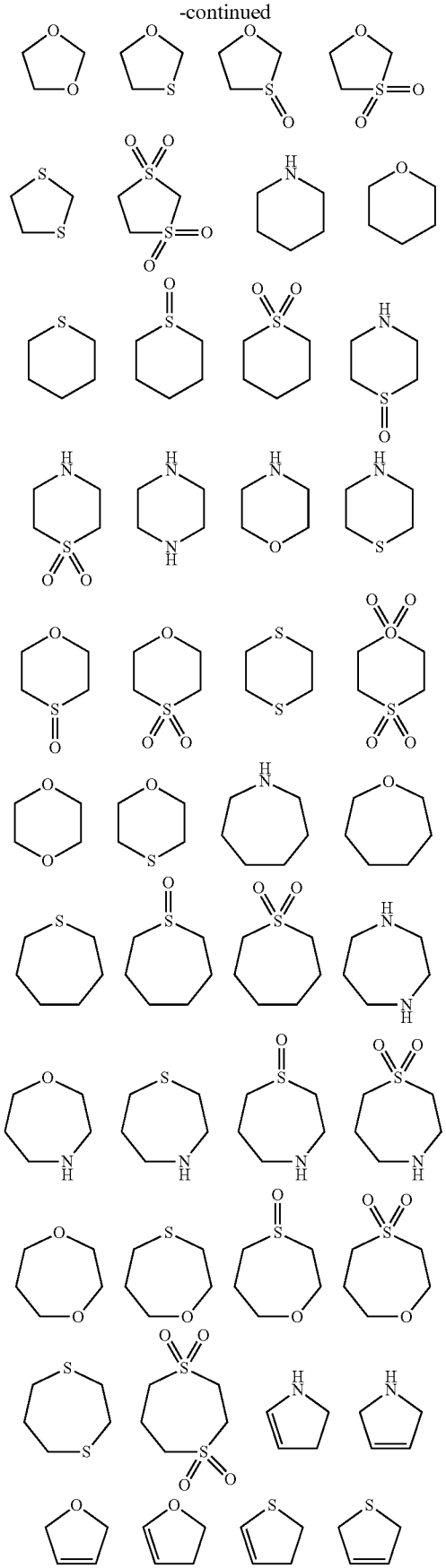

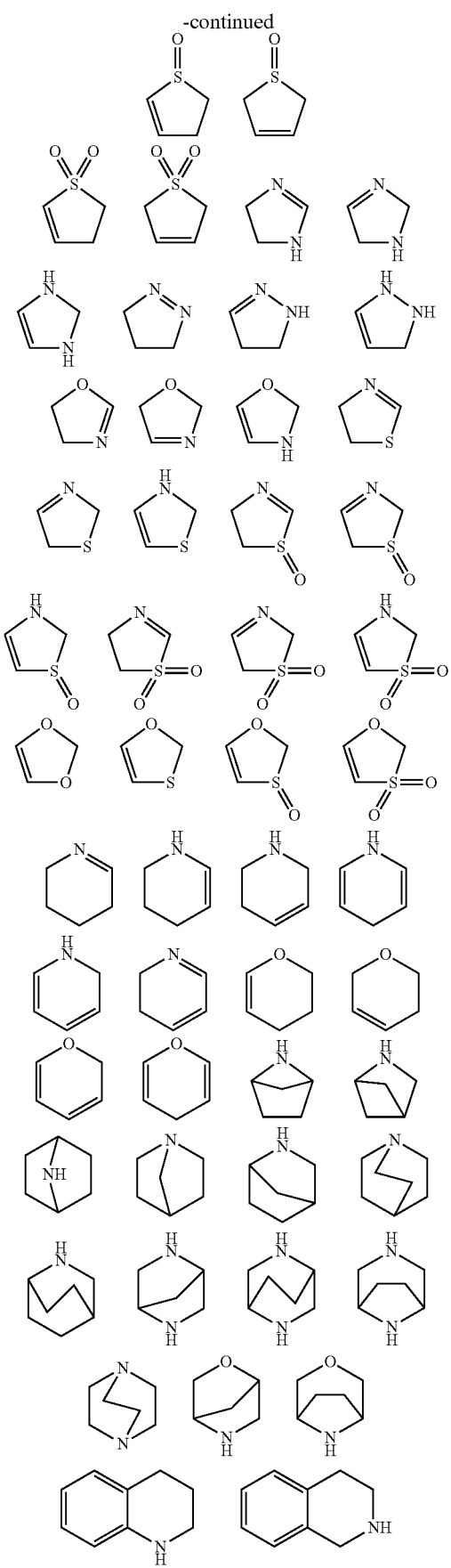
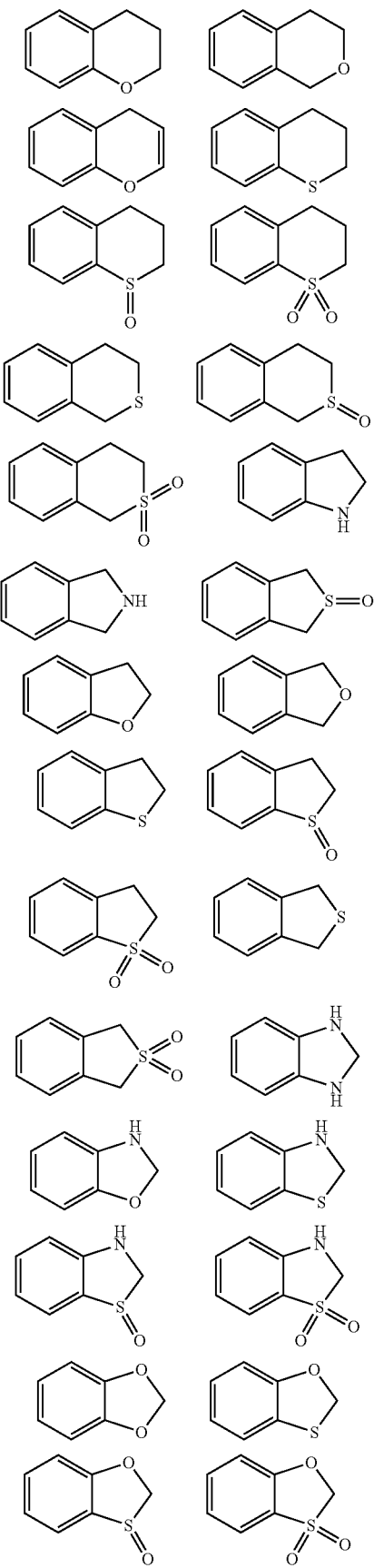

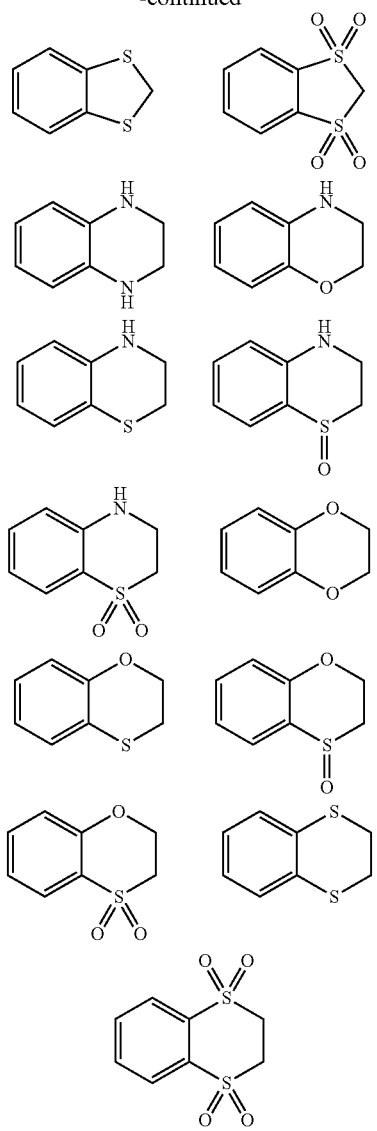

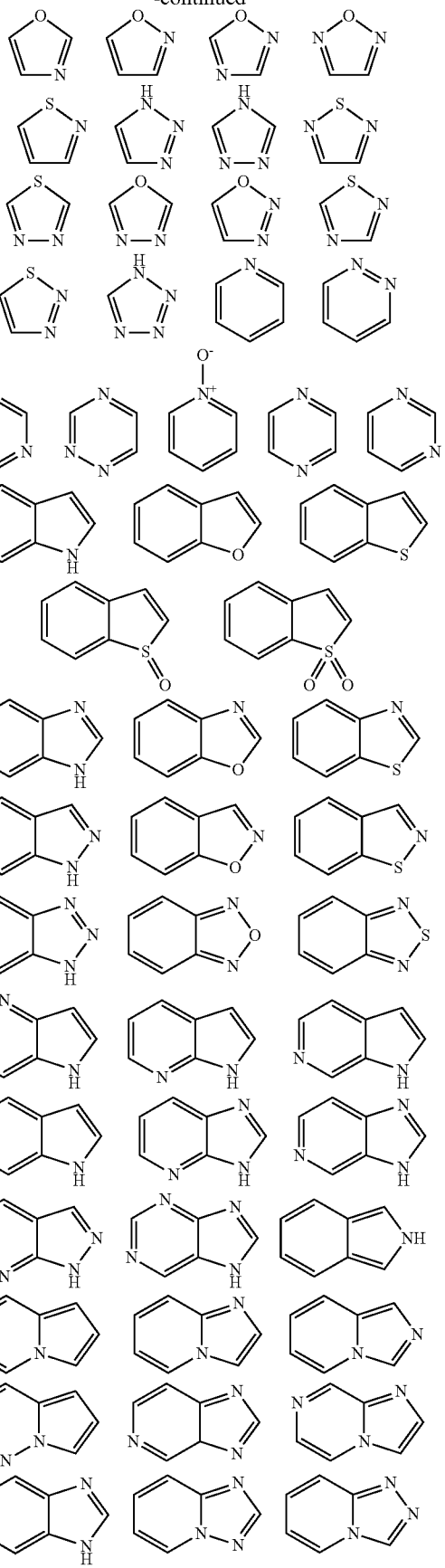

The term "heteroaryl" means a mono- or polycyclic-ring systems containing one or more heteroatoms selected from N, O or S(O)$_r$ with r=0, 1 or 2 wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

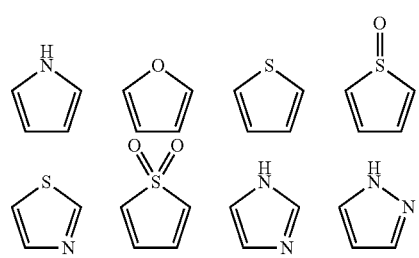

-continued

Many of the terms given above may be used repeatedly in the definition of a formula or group and in each case have one of the meanings given above, independently of one another.

PREFERRED EMBODIMENTS

The variables A, A' are independently from each other —$CH_2$— or —$CH_2$—$CH_2$—. Preferably A and A' are both —$CH_2$—$CH_2$— or A and A' are different from each other —$CH_2$— or —$CH_2$—$CH_2$—. Particularly preferred A and A' are both —$CH_2$—$CH_2$—.

The substituent R is selected from among —$NR^1R^2$, —$NR^3R^4R^{5(+)}Z_1^{(-)}$ and $OR^{13}$, preferably —$NR^1R^2$ or —$NR^3R^4R^{5(+)}X^{(-)}$, most preferably —$NR^1R^2$.

The substituent X denotes halogen, preferably Cl or Br; most preferably Cl.

The substituent $Z_1^{(-)}$ is halogen anion or an organic acid anion, preferably $CF_3COO^-$, $CH_3COO^-$, $CF$, $Br^-$ or $I^-$, particularly preferred $Cl^-$ or $I^-$.

The substituent $Z_2^{(-)}$ is halogen anion or an organic acid anion, $CF_3COO^-$, $CH_3COO-$, $Cl^-$ $Br^-$ or $I^-$, particularly preferred $Cl^-$ or $I^-$, The substituent $Z_3^{(-)}$ is halogen anion or an organic acid anion, $CF_3COO^-$, $CH_3COO-$, $Br^-$ or $I^-$, particularly preferred $Cl^-$ or $I^-$; The substituent $Z_4^{(-)}$ is halogen anion or an organic acid anion, $CF_3COO^-$, $CH_3COO-$, $Cl^-$ $Br^-$ or $I^-$, particularly preferred $Cl^-$ or $I^-$;

The substituents $R^1$, $R^2$ are selected independently from each other from among H, —$C(NH_2)NH$, —$CN(CH_3)_2N(CH_3)_2^+Z_2^-$, —$C_{1-3}$-alkyl, —$C_{2-4}$-alkyl-$N(CH_3)_2$, —$C_{1-3}$-alkyl-phenyl-$R^{12}$, —$C_{1-3}$-alkyl-COOH, —$C_{1-4}$-alkyl-CO—$Y^2$—$R^{11}$, —CO-phenyl-CO—O—$R^{13}$, —CO—$C_{1-4}$-alkyl, —CO—$C_{1-3}$-alkyl-$NR^6R^7$, —CO—$C_{1-3}$-alkyl-$N(CH_3)_3^+Z_3^-$, —CO—$C_{1-4}$-alkyl-$Y^1$—$R^9$, —CO—O—$C_{1-4}$-alkyl-$R^8$, —CO—NH—$C_{3-7}$-cycloalkyl, —CO—NH—$C_{1-4}$-alkyl, —$CH_2$—CO—O—$C_{1-3}$-alkyl, —$CH_2$—CO—O—$C_{1-3}$-alkyl-phenyl and —$SO_2$—$R^{10}$.

Especially preferred are the following combinations of $Y^1$ and $R^9$ within the substituent —CO—$C_{1-4}$-alkyl-$Y^1$—$R^9$:

If $Y^1$ denotes (a1), (d1) then $R^9$ denotes H, $C_{1-3}$-alkyl, =O.
If $Y^1$ denotes (b1), (c1) then $R^9$ denotes H or $C_{1-3}$-alkyl.
If $Y^1$ denotes (e1) or (j1) then $R^9$ is selected from among H, $C_{1-3}$-alkyl, =O, —OH, —O-Me-$N(CH_3)_2$ and —$N(CH_3)_3^+Z_4^-$.
If $Y^1$ denotes (f1), (g1), (h1), (i1) then $R^9$ denotes H or $C_{1-3}$-alkyl.

Especially preferred are the following combinations of $Y^2$ and $R^{11}$ within the substituent —$C_{1-4}$-alkyl-CO—$Y^2$—$R^{11}$:
If $Y^2$ denotes (a2), (d2) then $R^{11}$ denotes H, $C_{1-3}$-alkyl or —$O^-$.
If $Y^2$ denotes (b2), (c2) then $R^{11}$ denotes H or $C_{1-3}$-alkyl.
If $Y^2$ denotes (e2) then $R^{11}$ is selected from among H, $C_{1-3}$-alkyl, =O, —OH, —OMe-$N(CH_3)_2$ and —$N(CH_3)_3^+Z_4^-$.
If $Y^2$ denotes (f2), (g2), (h2) then $R^{11}$ denotes H or $C_{1-3}$-alkyl.

Preferably $R^1$ or $R^2$ are selected independently from each other from H, —$C_{1-4}$-alkyl-CO—$Y^2$—$R^{11}$ and —CO—$C_{1-4}$-alkyl-$Y^1$—$R^9$, more preferably $C_1$-alkyl-CO—$Y^2$—$R^{11}$ and —CO—$C_1$-alkyl-$Y^1$—$R^9$.

Also preferably $R^1$, $R^2$ independently from each other denote H, —$C(NH_2)NH$ or —$CN(CH_3)_2N(CH_3)_2^+Z_2^-$, more preferably —$C(NH_2)NH$.

Also preferably $R^1$ or $R^2$ are selected from among —$C_{1-3}$-alkyl, —$C_{2-4}$-alkyl-$N(CH_3)_2$, —$C_{1-3}$-alkyl-phenyl-$R^{12}$, —$C_{1-3}$-alkyl-COOH, —$CH_2$—CO—O—$C_{1-3}$-alkyl and —$CH_2$—CO—O—$C_{1-3}$-alkyl-phenyl, more preferably methyl, —$C_2$-alkyl-$N(CH_3)_2$, —$C_1$-alkyl-phenyl-$R^{12}$, —$C_1$-alkyl-COOH, —$C_1$-alkyl-CO—O-methyl and —$CH_2$—CO—O-benzyl.

Also preferably $R^1$, $R^2$ independently from each other are selected from among H, —CO-phenyl-CO—O—$C_{1-4}$—$R^{13}$, —CO—$C_{1-4}$-alkyl and —CO—$C_{1-3}$-alkyl-$NR^6R^7$, more preferably —CO-phenyl-CO—O-t-butyl, —CO-phenyl-CO—O-methyl, —CO-phenyl-CO—OH, —$CH_2$—$R^{13}$, —CO—$C_{1-4}$-alkyl and —CO—$C_{1-2}$-alkyl-$NR^6R^7$.

Also preferably $R^1$, $R^2$ independently from each other are selected from —CO—O—$C_{1-4}$-alkyl-$R^8$ or —$SO_2$—$R^{19}$, more preferably —CO—O—$CH_2$-alkyl-$R^8$ or —$SO_2$—$R^{10}$. Most preferably $R^1$ or $R^2$ denotes hydrogen.

Particularly preferred $R^1$ and $R^2$ form together with the nitrogen atom they are attached to an optionally substituted 4-7-membered heterocycle, containing at least one N and optionally one or more heteroatoms, selected from the group consisting of piperazino, morpholino, piperidino; diazepane; thiomorpholino, thiomorpholino-1-oxido, thiomorpholino-1,1-dioxid, pyrrolidino, wherein the nitrogen atoms may be substituted by a group selected from among phenyl, $C_{1-3}$-alkylsulfonyl-, $C_{1-3}$-alkyl and —C=O—$C_{1-3}$-alkyl.

Also particularly preferred $R^1$ and $R^2$ are together with the nitrogen atom they are attached to a 4-7-membered heterocycle containing 1 to 3 N-atoms, preferably 1 or 2 N-atoms.

The substituents $R^3$, $R^4$, $R^5$ denote independently from each other —$C_{1-3}$-alkyl, preferably methyl.

The substituent $R^6$ is selected from —$C_{1-3}$-alkyl, H, —$C_{2-4}$-alkyl-OH, —$CH_2$—CO—O—$C_{1-3}$-alkyl and —$CH_2$COOH; preferably —$C_{1-3}$-alkyl, H, —$C_2H_4$-alkyl-OH, The substituent $R^7$ is selected from —$C_{1-3}$-alkyl, —CO—O—$C_{1-3}$-alkyl, —$C_{2-4}$-alkyl-OH, H, —$CH_2$—CO—O—$C_{1-3}$-alkyl and —$CH_2$COOH; preferably H, $C_{1-3}$-alkyl and —$C_2$-alkyl-OH.

The substituent $R^8$ denotes H or phenyl.

The substituent $R^9$ is selected from H, —$C_{1-3}$-alkyl, OH, —$NR^6R^7$ and =O.

The substituent $R^N$ is selected from $C_{1-3}$-alkyl and an 5-8 membered optionally substituted, preferably 5 or 6-membered, N-containing nonaromatic heterocycle, preferably piperazino, 1-methylpiperazino, morpholino, piperidino, diazepane, 1-methyldiazepane; thiomorpholino, thiomorpholino-1-oxido, thiomorpholinon-1,1-dioxid and pyrrolidino, preferably piperazino, 1-methylpiperazino and morpholino.

The substituent $R^{11}$ is selected from H, $C_{1-3}$-alkyl, =O, —$N(CH_3)_2$ and —$N(CH_3)_3^+Z_4^-$.

The substituent $R^{12}$ is selected from H, halogen, —COOH, —$SO_3H$, —$PO(OC_{1-4}$-alkyl$)_2$, —$PO(OH)_2$— and $PO(OC_{1-4}$-alkyl)OH optionally substituted at the 2, 3 or 4 position of the $C_{1-4}$-alkyl group by —$N(C_{1-3}$-alkyl$)_2$ or —$N(C_{1-3}$-alkyl$)_3^+Z_4^-$, —$NH(C_{1-3}$-alkyl$)_2$ and —$N(C_{1-3}$-alkyl$)_3^+Z_4^-$. Preferably $R^{12}$ denotes H or halogen.

The substituent $R^{13}$ denotes H or $C_{1-4}$-alkyl, preferably H, methyl or t-butyl.

The substituent $Y^1$ is selected from an optionally substituted 5- to 8-membered N-containing nonaromatic heterocycle, —$N(C_{1-3}$-alkyl$)$-$C_{2-4}$-alkyl-$N(C_{1-3}$-alkyl$)_2$ and —$N(C_{1-3}$-alkyl$)$-$C_{2-4}$-alkyl-$N^+(C_{1-3}$alkyl$)_3Z_1^{(-)}$.

Preferably the substituent $Y^1$ is an optionally substituted 5- to 8-membered N-containing nonaromatic heterocycle.

More preferably $Y^1$ is selected from a linker of formula (a1) to (j1).

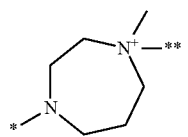
(a1)

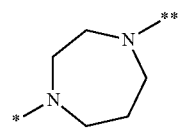
(b1)

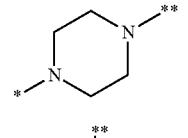
(c1)

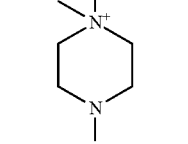
(d1)

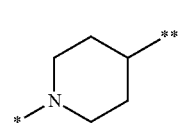
(e1)

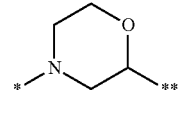
(f1)

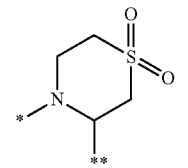
(g1)

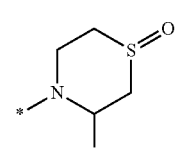
(h1)

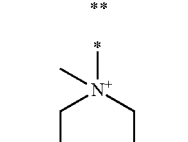
(i1)

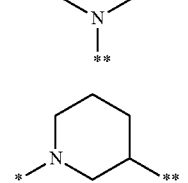
(j1)

wherein
* denotes the attachment point to the alkyl moiety of —CO—$C_{1-4}$-alkyl-*
** denotes the attachment point to $R^9$ The substituent $Y^2$ denotes an optionally substituted 5- to 8-membered N-containing nonaromatic heterocycle, preferably a 5- to 8-membered N-containing nonaromatic heterocycle substituted by =O.

Preferably $Y^2$ is selected from among a linker of formula (a2) to (i2), more preferably from among a linker of formula (a2), (b2), (c2) and (d2).

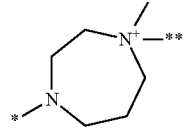
(a2)

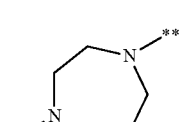
(b2)

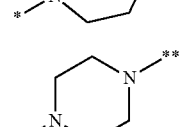
(c2)

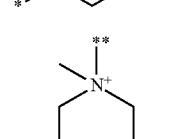
(d2)

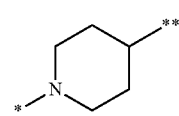
(e2)

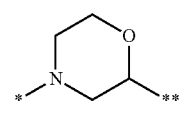
(f2)

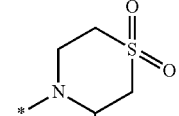
(g2)

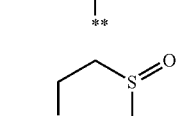
(h2)

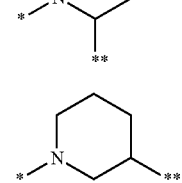
(i2)

wherein
* denotes the attachment point to the carbonyl moiety of
  —C$_{1-4}$-alkyl-CO—*
** denotes the attachment point to R$^{11}$ Preparation Where no salt forms of compounds are specified, the compound may exist as a free base or a salt, depending on the synthesis conditions and the procedure of the workup and purification applied. The skilled person will appreciate that the compound is not limited to the free base or a certain salt form. Where salt forms of compounds are specified, the stoichiometry of the counterion is usually omitted. The skilled person will appreciate that the compound is not limited to the mono salt form and that it may exist as a disalt, trisalt or other compound:counterion stoichiometries. Furthermore, the skilled person will appreciate that such is compound may unexpectedly exist as a free base or as a salt with a different counterion, depending on the synthesis conditions and the procedure of the workup and purification applied. Solely for the purpose of yield determination, an estimate of the nature of the counterion and of compound:counterion stoichiometry is made (as indicated by the formula given).

The compounds according to the invention may be obtained using methods of synthesis which are known to the one skilled in the art and described in the literature of organic synthesis. If a substituent is not compatible with the synthetic methods described herein, the substituent may be protected with a suitable protecting group. General methods for functional groups protection and deprotection steps are described e.g. in: Greene, T. W. and Wuts, P. G. M. (eds.): *Protective Groups in Organic Synthesis*, third edition 1999; John Wiley and Sons, inc.

Preferably the compounds are obtained analogously to the methods of preparation explained more fully hereinafter, in particular as described in the experimental section.

Scheme 1:

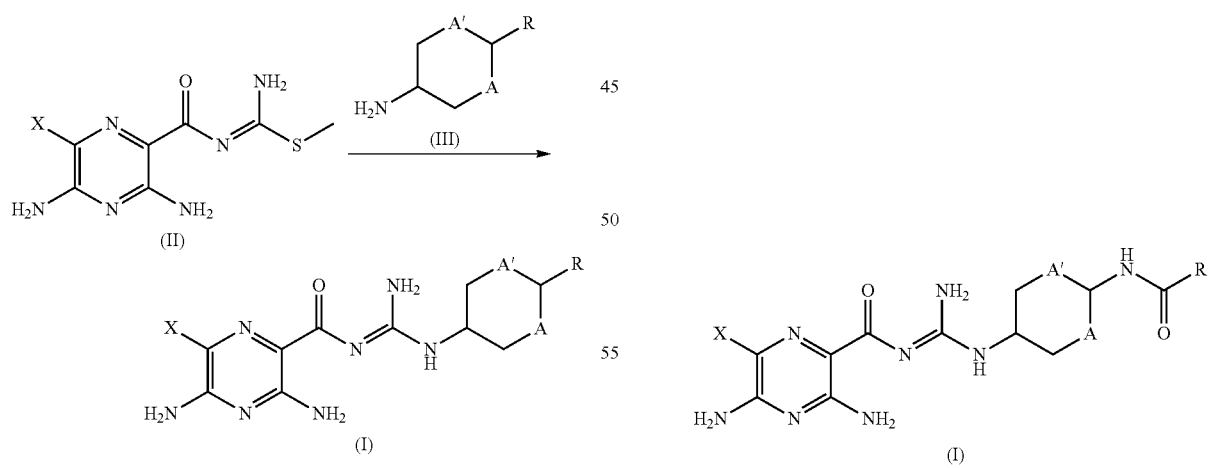

As shown in scheme 1 compounds of general formula (I) can be prepared by reacting S-methylisothioureas of formula (II) with a primary amines of formula (III) in a solvent like THF, acetonitrile or DMF or in a solvent mixture, preferably in the presence of a base, especially when the primary amine (III) is applied as an acid addition salt, preferably at temperature between r.t. and boiling point of the solvent.

Scheme 2:

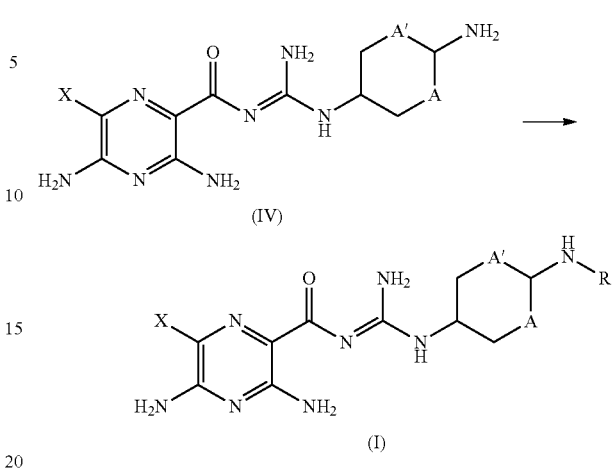

As shown in scheme 2 another method for preparation of compounds if formula (I) is alkylation of compounds of general formula IV with a suitable alkyl derivative R-LG (wherein the leaving group LG is preferably I, Cl, Br, OMesyl, or OTosyl), in the presence of a base such as K$_2$CO$_3$ in an appropriate solvent such as DMF or acetone at room temperature or elevated temperature as shown in scheme 2.

Scheme 3:

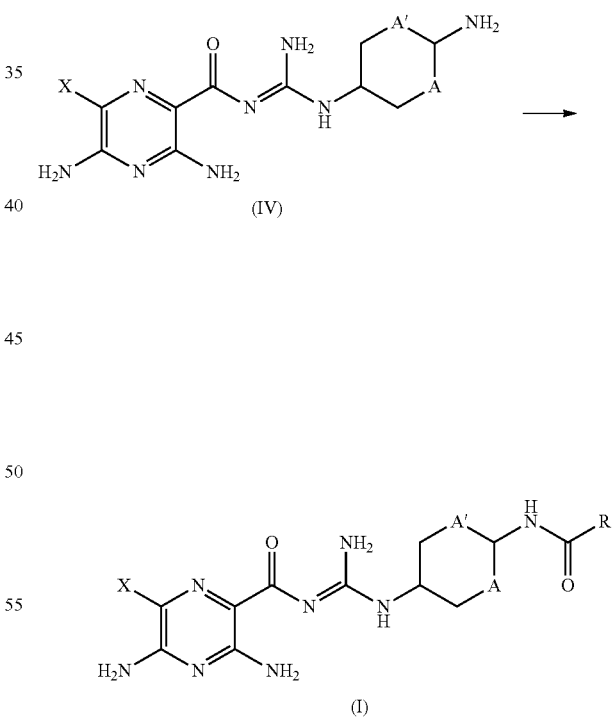

As shown in scheme 3 compounds of formula (I) with an amide group can be prepared by acylating the corresponding amine IV with an carboxylic acid using a coupling agent such as HATU or using an activated carboxylic acid derivative such as an carboxylic acid halide and a base such as TEA at room temperature or elevated temperature in a nonaqueous solvent.

Scheme 4:

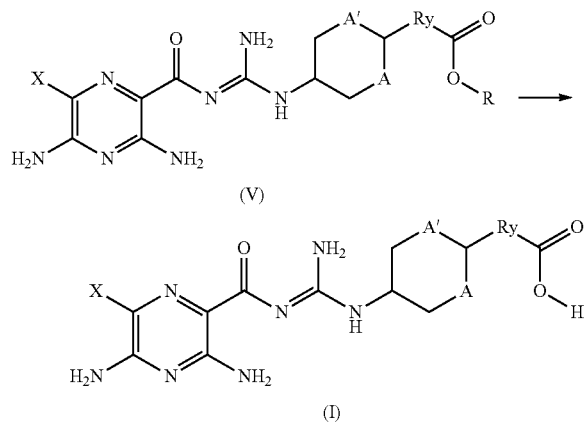

As shown in scheme 4 compounds of formula (I) with a Ry group incorporating an acid can be prepared by hydrolyzing the corresponding ester V using a base such as NaOH, KOH or LiOH at room temperature or elevated temperature in an aqueous solvent.

Scheme 5:

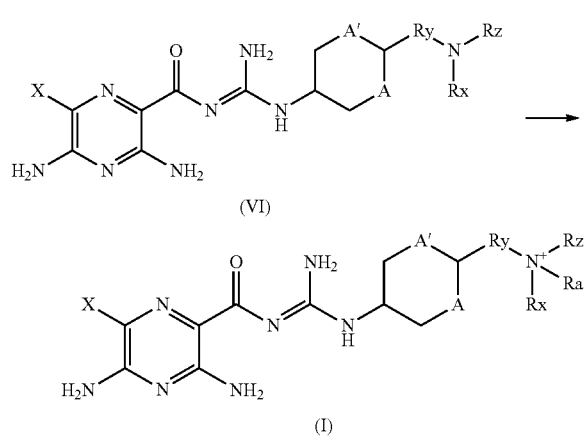

As shown in scheme 5 compounds of formula (I) with a Ry group incorporating a quaternary amine can be prepared by alkylating the corresponding amine using an alkylating agent R-LG (wherein the leaving group LG is preferably I, Cl, Br, OMesyl, or OTosyl) e.g. MeI or $Me_2SO_4$ at room temperature or elevated temperature in an appropriate solvent in the presence or without an appropriate base.

Scheme 6:

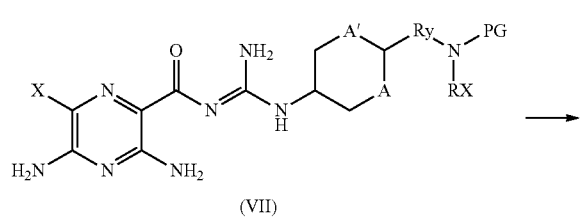

-continued

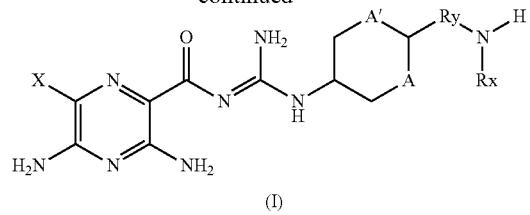

As shown in scheme 6 amines of general formula (I) can be prepared by removing the respective protecting group PG. Suitable protecting groups PG in (VII) are e.g. BOC, FMOC and phthaloyl which can be removed by standard acidic conditions e.g. using acids like TFA, standard basic conditions using bases such as morpholine or hydrazine respectively.

Scheme 7:

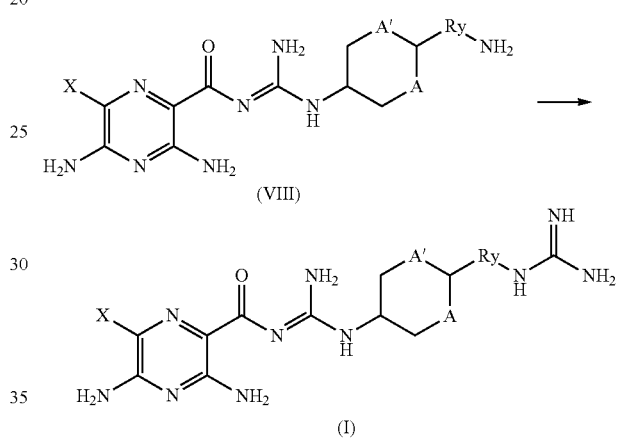

As shown in scheme 7 compounds of formula (I) with a Ry group incorporating a guanidion group can be prepared by reacting the corresponding amine VIII with S-methylisothiourea hydrochloride or 1H-1,2,4-triazole-1-carboxamidine hydrochloride and a base such as DIPEA in an appropriate solvent at room temperature or a elevated temperature.

Scheme 8:

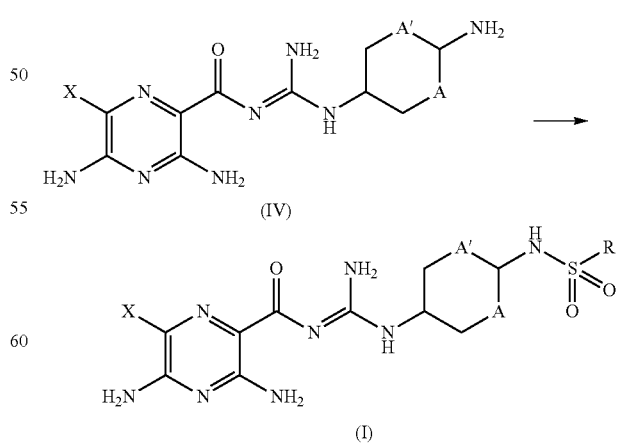

As shown in scheme 8 compounds of formula (I) with a sulfonamido or a sulfamoyl group can be prepared by reacting the corresponding amine with an alkyl or aryl sulfonic acid chloride or an alkyl or aryl sulfamoylchloride and a base such as TEA at room temperature or elevated temperature in a nonaqueous solvent.

Scheme 9:

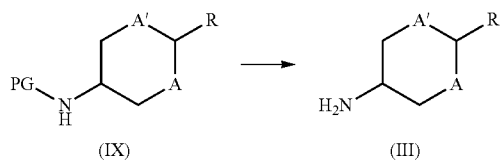

As shown in scheme 9 when not commercially available, amines of general formula (III) can be prepared from compounds of general formula (IX) by removal of the respective protecting group, preferably the BOC, phthaloyl or FMOC protecting group which can be removed by standard acidic or basic conditions, respectively.

Scheme 10:

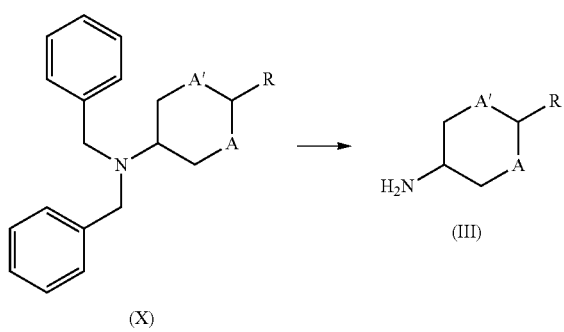

Alternatively benzyl groups can be used as protecting groups which can be removed by hydrogenation as shown in scheme 10.

Compounds of general formula (IX) or (X) (Scheme 9 or 10) can be modified using methods of synthesis which are known to the one skilled in the art and described in the literature of organic synthesis, preferably by functional group protection or deprotection steps, esterifications, amidations, reductions, alkylations or oxidations.

Scheme 11:

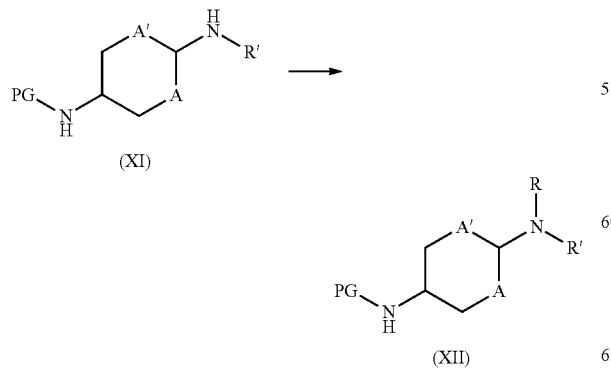

Intermediates of general formula (IX) with a R group incorporating a secondary (R'=H) or tertiary amine (R'=alkyl or amide or sulfonamide (R=CO-alkyl, —CO-aryl, —SO$_2$-alkyl, —SO$_2$aryl) can be prepared by using an alkylating agent R-LG (wherein the leaving group LG is preferably I, Cl, Br, OMesyl, or OTosyl) such as R—Br or R—Cl for alkylation of XI at room temperature or elevated temperature in an appropriate solvent in the presence or without an appropriate base as shown in scheme 11.

Scheme 12:

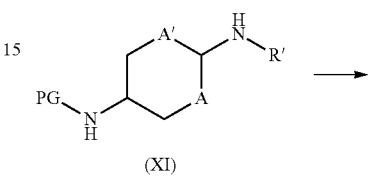

Compounds of formula (IX) with a sulfonamide or a sulfamoyl group can be prepared by reacting the corresponding amine XI with an alkyl or aryl sulfonic acid chloride or an alkyl or aryl sulfamoylchloride and a base such as TEA at room temperature or elevated temperature in a nonaqueous solvent as shown in scheme 12.

Scheme 13:

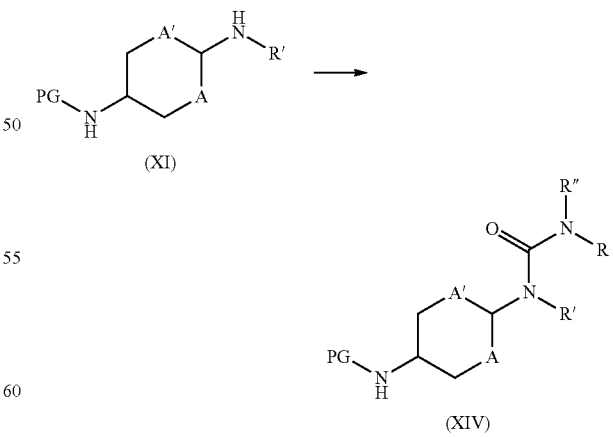

As shown in scheme 13 compounds of formula (XIV) with an urea group can be prepared by reacting the corresponding amine XI with an alkyl isocyanate at room temperature or elevated temperature in a nonaqueous solvent.

Scheme 14:

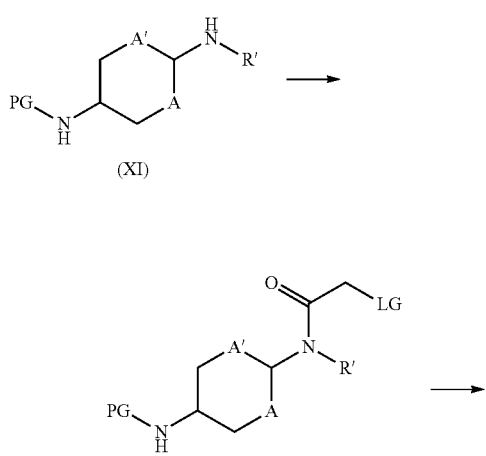

As shown in scheme 14 intermediate of general formula (XV) with an glycineamido group can be prepared by reacting the corresponding amine XI with chloro-acetyl chloride at room temperature or elevated temperature in a nonaqueous solvent in the presence of a base. Then the intermediate is reacted with a substituted amine.

Scheme 15:

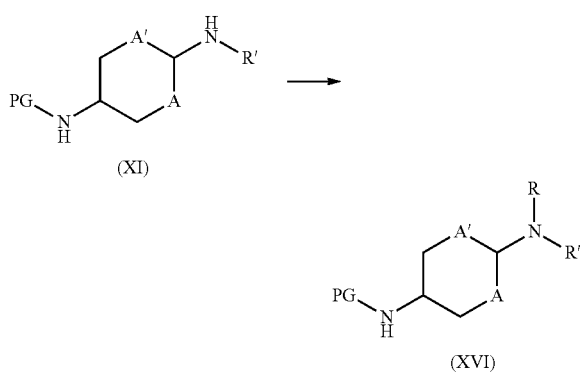

As shown in scheme 15 intermediates of general formula (XVI) with a secondary (R'=H) or tertiary amine (R'=alkyl) can be prepared by reductive alkylation of the corresponding amine using an alkyl or aryl aldehyde and a reducing agend such as NaBH$_4$ or sodium triacetoxy borohydride at room temperature or elevated temperature in an appropriate solvent.

Scheme 16:

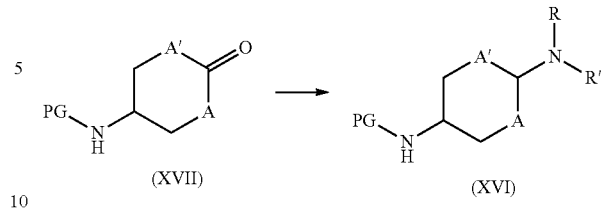

An alternative procedure to get compounds of formula (XVI) is by reductive alkylation of the corresponding cyclohexanone (XVII) using an alkyl or aryl amine and a reducing agend such as NaBH4 or sodium triacetoxy borohydride at room temperature or elevated temperature in an appropriate solvent as shown in scheme 16.

SYNTHESIS OF INTERMEDIATES

Intermediate A.1

3,5-diamino-6-chloropyrazine-2-carboxylic acid

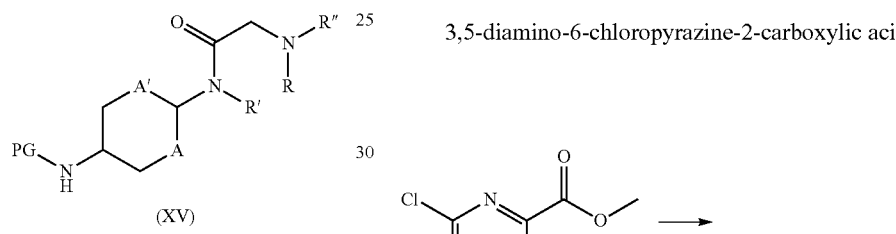

A mixture of methyl 3,5-diamino-6-chloropyrazine-2-carboxylate (100 g; 494 mmol), methanol (1 l) and NaOH (6 mol/l in water; 240 mL; 1.44 mol) is refluxed for 3 h. The mixture is allowed to cool to r.t. and then neutralized by addition of hydrochloric acid (6 mol/l in water; approx. 240 mL). Water (200 mL) is added. The precipitate formed is filtered off with suction, washed with water and dried at 60° C.

$C_5H_5ClN_4O_2$ ESI Mass spectrum: m/z=189 [M+H]$^+$; m/z=187 [M−H]$^-$

Intermediate A.2

3,5-Diamino-6-bromopyrazine-2-carboxylic acid is prepared from methyl 3,5-diamino-6-bromopyrazine-2-carboxylate (which is prepared from methyl 3,5-diamino-6-chloropyrazine-2-carboxylate as described in J. Med. Chem.

10 (1967) 66-75) analogously to the procedure described for the synthesis of intermediate A.1

Intermediate B.1

1-(tert-Butylcarbamoyl)prop-1-en-2-yl 3,5-diamino-6-chloropyrazine-2-carboxylate

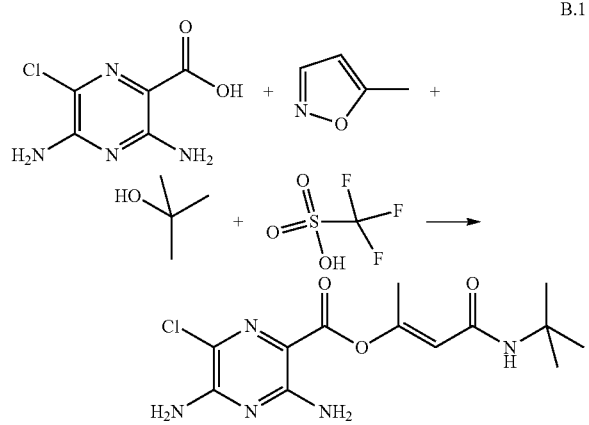

B.1

Stage 1:

A mixture of tert-butanol (21.0 mL; 226 mmol) and 5-methylisoxazole (18.0 mL; 221 mmol) is cooled with an ice-bath. Trifluoromethanesulphonic acid (20.0 mL; 221 mmol) is added dropwise with continued cooling. The resulting mixture is stirred for 1 h without further cooling.

Stage 2:

To a solution or suspension of 3,5-diamino-6-chloropyrazine-2-carboxylic acid (intermediate A.1; 14.0 g; 74.2 mmol) and triethylamine (31.0 mL; 222 mmol) in DMF (100 mL) is added the mixture prepared in stage 1. The resulting mixture is stirred for 4 h at r.t. Ice-water is added with stirring. The precipitate formed is filtered off with suction, washed with water and dried at 65° C. to yield the title compound.

$C_{13}H_{18}ClN_5O_3$ ESI Mass spectrum: m/z=328 [M+H]+; m/z=326 [M−H]− TLC (Silica; DCM/MeOH 9:1): $R_f$=0.4

Intermediate B.2

1-(2-Methyl-2-butyl-carbamoyl)prop-1-en-2-yl 3,5-diamino-6-bromopyrazine-2-carboxylate

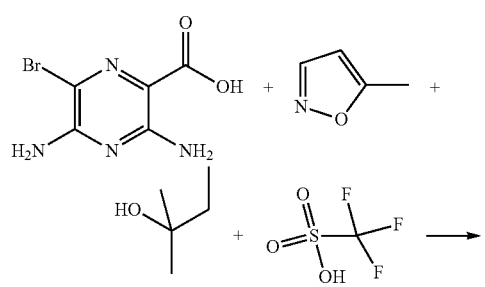

B.2

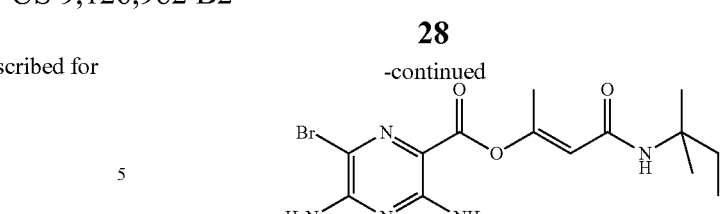

Stage 1:

A mixture of 2-methyl-2-butanol (5.75 mL; 51 mmol) and 5-methylisoxazole (4.42 mL; 51 mmol) is cooled with an ice-bath. Trifluoromethanesulphonic acid (4.84 mL; 54 mmol) is added dropwise with continued cooling. The resulting mixture is stirred over night without further cooling.

Stage 2:

To a solution or suspension of 3,5-diamino-6-bromopyrazine-2-carboxylic acid (Intermediate A.2; 5.00 g; 21.5 mmol) and triethylamine (7.48 mL; 54 mmol) in DMF (50 mL) cooled with an ice-bath is added dropwise the mixture prepared in stage 1. The resulting mixture is stirred for 4 h at r.t., then poured on ice-water. The precipitate formed is filtered off with suction, washed with water and dried at 50° C. to yield the title compound.

$C_{14}H_{20}BrN_5O_3$ ESI Mass spectrum: m/z=386 [M+H]+; m/z=384 [M−H]−

Intermediate C.1

3,5-diamino-6-chloro-N-[(methylsulfanyl)methanimidoyl]pyrazine-2-carboxamide

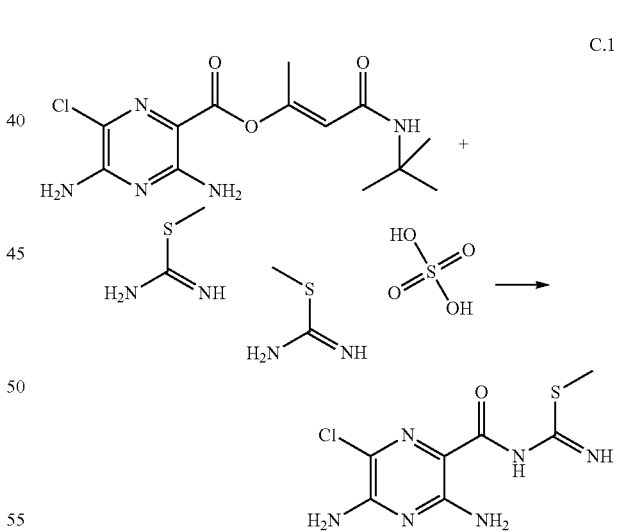

C.1

To NaOH (1 mol/l in water; 9.2 mL; 9.2 mmol) is added S-methylisothiourea sulphate (1.78 g; 6.1 mmol. The mixture is stirred until complete solution is achieved. TBME/THF (1:1; 30 mL) and then 1-(tert-butylcarbamoyl)prop-1-en-2-yl 3,5-diamino-6-chloropyrazine-2-carboxylate (Intermediate B.1; 2.00 g; 6.10 mmol) are added and the mixture is stirred at r.t. over night, then water (6 mL) is added. The precipitate formed is filtered off with suction, washed successively with water, methanol and then with diethyl ether and then dried at 50° C. to yield the title compound.

C₇H₉ClN₆OS ESI Mass spectrum: m/z=261 [M+H]+; m/z=259 [M−H]⁻

Intermediate C.2

3,5-diamino-6-bromo-N-[(methylsulfanyl)methanimidoyl]pyrazine-2-carboxamide

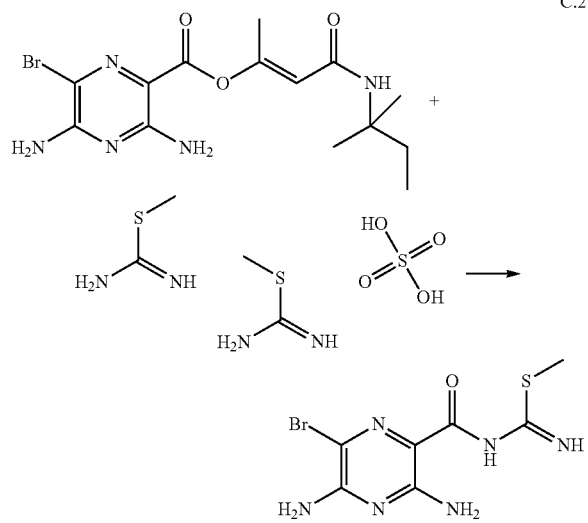

Intermediate I.1

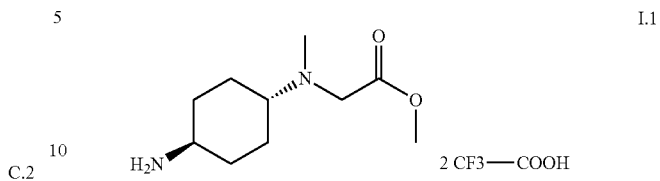

A mixture of trans-(4-methylamino-cyclohexyl)-carbamic acid tert-butylester (100.0 mg; 0.44 mmol), bromo-acetic acid methylester (46.0 µL; 0.49 mmol) and potassium carbonate (90.7 mg; 0.66 mmol) in ACN (1 mL) is stirred at r.t. over night. The insoluble material is filtered off and the solvent is removed. The residue is taken up in DCM and washed with water. The organic layer is separated and the solvent is removed. The residue is purified by RP HPLC (modifier: NH₃). The residue is taken up in TFA (50% in DCM) and stirred at r.t. for 1 hour. The solvent is removed.

C₁₀H₂₀N₂O₂*2C₂HF₃O₂

The following compounds are prepared accordingly using the respective amine and the halogenide as indicated. Due to conditions applied, the synthesis may yield a free base, a hydrochloride or dihydrochloride salt, a zwitterion or other salt forms which can be applied equally to the syntheses of example compounds as described above.

| Intermediate | | respective amine | Respective halogenide | Synthesis comment |
|---|---|---|---|---|
| I.2 | (structure) | trans-(4-amino-cyclohexyl)-carbamic acid tert-butylester | (structure) | No purification by RP HPLC |
| I.3 | (structure) | trans-(4-methylamino-cyclohexyl)-carbamic acid tert-butylester | (structure) | No purification by RP HPLC |

To NaOH (1 mol/l in water; 30 mL; 30 mmol) is added S-methylisothiourea sulphate (5.42 g; 19.5 mmol. The mixture is stirred until complete solution is achieved. TBME/THF (1:1; 100 mL) and then 1-(2-methyl-2-butyl-carbamoyl)prop-1-en-2-yl 3,5-diamino-6-bromopyrazine-2-carboxylate (Intermediate B.2; 7.52 g; 19.5 mmol) are added and the mixture is stirred at r.t. over night, then water (100 mL) is added. The precipitate formed is filtered off with suction, washed with THF/water (1:2) and then dried at 50° C. to yield the title compound.

C₇H₉BrN₆OS ESI Mass spectrum: m/z=305 [M+H]+

Intermediate II.1

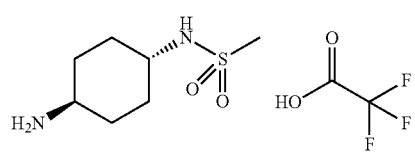

Stage 1: A mixture of trans-(4-aminocyclohexyl)-carbamic acid tert-butylester (215.0 mg; 1.00 mmol) and methane sulfonyl chloride (85.8 μL; 1.10 mmol) in DCM (10 mL) is stirred at r.t. for 5 minutes. TEA (160.0 μL; 1.15 mmol) is added and the mixture is stirred at r.t. for 2 hours. The mixture is diluted with aqueous KHSO$_4$ (2M). The organic layer is separated and washed again with aqueous NaHCO$_3$ (half-saturated). The organic layer is separated and the solvent is removed.

$C_{12}H_{24}N_2O_4S$

Stage 2: Intermediate II.1 stage 1 (90.0 mg; 0.31 mmol) and TFA/DCM (2/1; 3 mL) is stirred at r.t. for 2 hours. The solvent is removed. The resulting residue is used without further purification.

$C_7H_{16}N_2O_2S*C_2HF_3O_2$

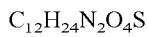

Intermediate III.1

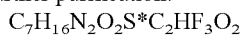

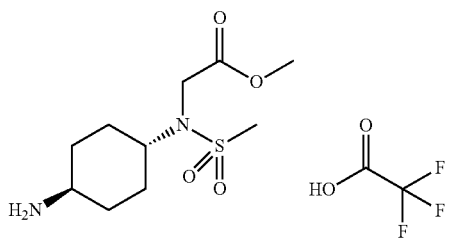

A mixture of trans-(4-aminocyclohexyl)-carbamic acid tert-butylester (215.0 mg; 1.00 mmol) and TEA (160.0 μL; 1.15 mmol) in DCM (15 mL) is stirred at r.t. Methane sulfonyl chloride (85.8 μL; 1.10 mmol) is added and the mixture is stirred at r.t. for 2 hours. LiHMDS (1M in THF; 1.20 mL; 1.20 mmol) and bromo-acetic acid methyl ester (115.0 μL; 1.21 mmol) are added. The mixture is stirred at r.t. over night. The mixture is diluted with water and the organic layer is separated. The solvent is removed. The residue is taken up in TFA (25% in DCM) and stirred at r.t. for 4 hours. The solvent is removed.

$C_{10}H_{20}N_2O_4S*C_2HF_3O_2$

Intermediate IV.1a

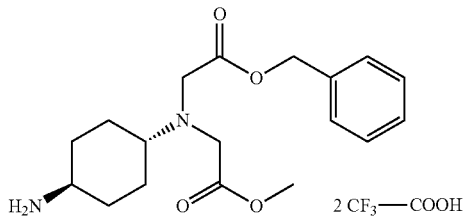

A mixture of trans-(4-aminocyclohexyl)-carbamic acid tert-butylester (1.07 g; 5.00 mmol), bromo-acetic acid methy ester (535.8 μL; 5.66 mmol) and potassium carbonate (1.10 g; 7.97 mmol) in ACN (30 mL) is stirred at r.t. for 2 hours. Then another portion of potassium carbonate (1.10 g; 7.97 mmol) and bromo-acetic acid benzyl ester (860.0 μL; 5.50 mmol) are added. After stirring at r.t. over night insoluble material is filtered off. The residue is purified by RP HPLC (modifier: TFA). The residue is taken up in TFA (50% in DCM; 30 mL) and stirred at r.t. for 2 hour. The solvent is removed.

$C_{18}H_{26}N_2O_4*2C_2HF_3O_2$

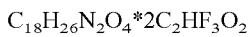

Intermediate IV.1b

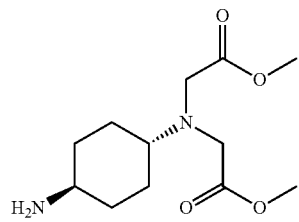

This molecule is a side product of the reaction described for intermediate IV.1a. It was obtained after chromatography and further removal of the protection group.

$C_{17}H_{30}N_2O_6$

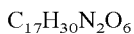

Intermediate V.1

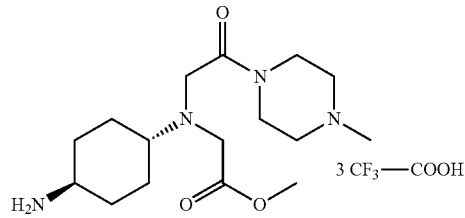

Stage 1: A mixture of Intermediate IV.1a (1.20 g; 2.76 mmol) and palladium on charcoal (200.0 mg) in methanol (50 mL) is hydrogenated in a Parr apparatus (r.t.; 50 psi; 3 hours). The catalyst is filtered off. The solvent is removed. The residue is stirred in diethyl ether, filtered off and dried.

$C_{16}H_{28}N_2O_6$

Stage 2: A mixture of Intermediate V.1 stage 1 (100.0 mg; 0.26 mmol), TBTU (90.0 mg; 0.28 mmol) and TEA (55.0 μL; 0.39 mmol) in DCM (3 mL) is stirred at r.t. for 30 minutes. N-Methylpiperazine (35.0 μL; 0.23 mmol) is added. After stirring for 4 hours the mixture is diluted with DCM and water. The organic layer is separated and evaporated. The residue is taken up in TFA (25% in DCM) and stirred at r.t. over night. The solvent is removed.

$C_{16}H_{30}N_4O_3*3C_2HF_3O_2$

The following compounds are prepared accordingly using the respective amine as indicates ed. Due to conditions applied, the synthesis may yield a free base, a hydrochloride or dihydrochloride salt, a zwitterion or other salt forms which can be applied equally to the syntheses of example compounds as described above.

| Intermediate | | respective amine |
|---|---|---|
| V.2 | (structure) | 4-methylpiperidine |
| V.3 | (structure) | thiomorpholine-1,1-dioxide |

Intermediate VI.1

VI.1 (structure)

A mixture of trans-(4-aminocyclohexyl)-carbamic acid tert-butylester (200.0 mg; 0.93 mmol) and 4-fluoro-benzaldehyde (120.0 µL; 1.14 mmol) in methanol (5 mL) is stirred for 1 hour at reflux. The mixture is cooled to r.t. NaBH$_4$ (50.0 mg; 1.32 mmol) is added and the mixture is stirred at r.t. over night. Methyl iodide (70.0 µL) and DIPEA (240.0 µL; 1.40 mmol) are added. The mixture is stirred at r.t. for 4 hours. Additional methyl iodide (70.0 µL) is added. After stiffing over night once again methyl iodide (140.0 µL) and DIPEA (480 µL) is added. The mixture is stirred for 4 hours. The solvent is removed and the residue is purified by RP HPLC (modifier: NH$_3$). The residue is diluted in TFA (25% in DCM) and stirred at r.t. for 2 hours. The solvent is evaporated.

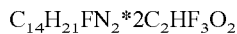

The following compounds are prepared accordingly using the respective aldeyhde as indicated. Due to conditions applied, the synthesis may yield a free base, a hydrochloride or dihydrochloride salt, a zwitterion or other salt forms which can be applied equally to the syntheses of example compounds as described above.

| Intermediate | | respective aldehyde |
|---|---|---|
| VI.2 | (structure) | 2-fluoro-benzaldehyde |

Intermediate VII.1

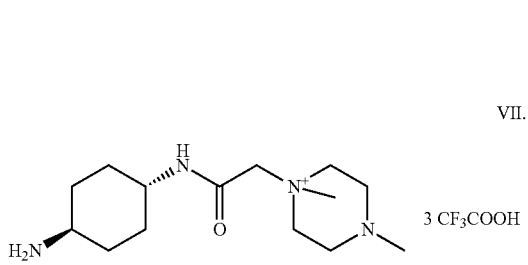

A mixture of trans-(4-aminocyclohexyl)-carbamic acid tert-butylester (300.0 mg; 1.40 mmol) and TEA (290.0 µL; 2.09 mmol) in DCM (20 mL) is cooled in an ice bath. Chloroacetyl chloride (120.0 µL; 1.51 mmol) in DCM (10 mL) is added drop wise. The mixture is diluted with water. The organic layer is separated, dried and evaporated. The residue is taken up in THF and 1,4-dimethylpiperazine (1.00 mL; 7.39 mmol) is added. After stirring at 60° C. over night the mixture is purified by RP HPLC (modifier: TFA).

$C_{14}H_{29}N_4O*2C_2HF_3O_2*C_2F_3O_2$

Intermediate VIII.1

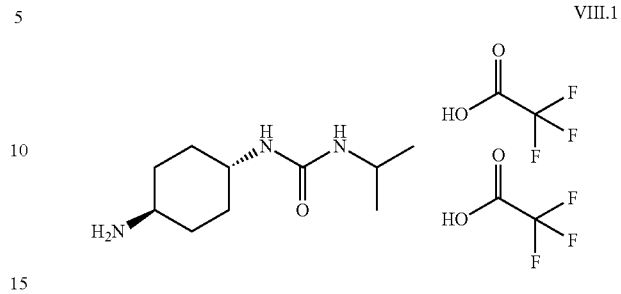

A mixture of trans-(4-aminocyclohexyl)-carbamic acid tert-butylester (150.0 mg; 0.70 mmol) and isopropyl isocyanate (65.5 mg; 0.77 mmol) in THF (10 mL) is stirred at r.t. for 1 hour. The solvent is removed and the residue is stirred in diethyl ether, filtered off and dried. The residue is diluted in TFA (25% in DCM) and stirred at r.t. over night. The solvent is evaporated.

$C_{10}H_{21}H_{21}N_3O*2C_2HF_3O_2$

ESI Mass spectrum: m/z=298 [M−H]−

The following compounds are prepared accordingly using the respective isocyanate as indicated. Due to conditions applied, the synthesis may yield a free base, a hydrochloride or dihydrochloride salt, a zwitterion or other salt forms which can be applied equally to the syntheses of example compounds as described above.

| Intermediate | | respective isocyanate | ESI Mass spectrum |
|---|---|---|---|
| VIII.2 | 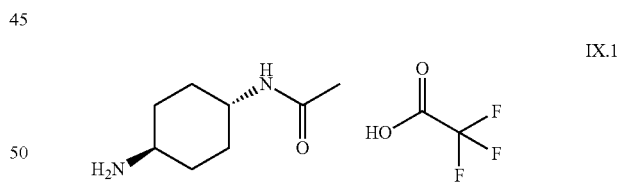 | Cyclohexane isocyanate | 340 (M + H)+ |

Intermediate IX.1

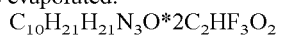

A mixture of trans-(4-aminocyclohexyl)-carbamic acid tert-butylester (150.0 mg; 0.70 mmol) and DIPEA (479.3 µL; 2.80 mmol) in DCM (10 mL) is stirred at r.t. for 5 minutes. Acetyl chloride (49.7 µL; 0.70 mmol) is added. After stiffing over night the mixture is diluted with water and DCM. The organic layer is separated and the solvent is removed. The residue is diluted in TFA (25% in DCM; 10 mL) and stirred at r.t. over night. The solvent is evaporated.

$C_8H_{16}N_2O*C_2HF_3O_2$

ESI Mass spectrum: m/z=157 [M+H]+

The following compounds are prepared accordingly using the respective chloride as indicated. Due to conditions applied, the synthesis may yield a free base, a hydrochloride or dihydrochloride salt, a zwitterion or other salt forms which can be applied equally to the syntheses of example compounds as described above.

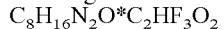

| Intermediate | | respective chloride | Synthesis comment |
|---|---|---|---|
| IX.2 | 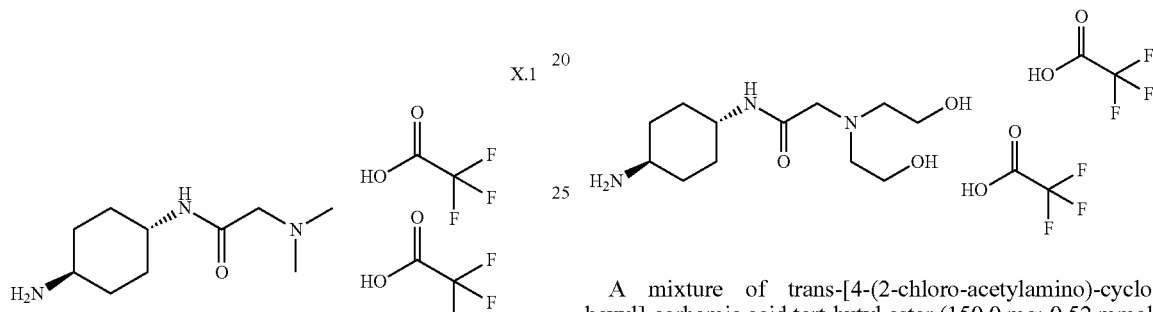 | isovaleryl chloride | The resulting intermediate is not purified by extraction, but by stirring in diethyl ether |

Intermediate X.1

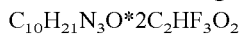

A mixture of N,N-dimethylglycine (62.6 mg; 0.61 mmol), HATU (230.6 mg; 0.61 mmol) and TEA (226.4 µL; 1.63 mmol) in DMF (3 mL) is stirred at r.t. for 45 minutes. trans-(4-Aminocyclohexyl)-carbamic acid tert-butylester (100.0 mg; 0.47 mmol) is added. After stirring for 1.5 hours the mixture is purified by RP HPLC (modifier: TFA). The solvent removed. The residue is diluted in TFA (25% in DCM; 6 mL) and stirred at r.t. over night. The solvent is evaporated.

$C_{10}H_{21}N_3O*2C_2HF_3O_2$

ESI Mass spectrum: m/z=200 [M+H]+

Intermediate XI.1

A mixture of trans-[4-(2-chloro-acetylamino)-cyclohexyl]-carbamic acid tert-butyl ester (150.0 mg; 0.52 mmol; prepared from trans-(4-aminocyclohexyl)-carbamic acid tert-butylester and chloro-acetyl chloride analogous to intermediate VII.1), 2-(2-hydroxyethylamino)ethanol (105.1 mg; 1.00 mol), potassium carbonate (276 mg; 2.00 mmol) and potassium iodide (20.0 mg; 0.12 mmol) in acetone (10 mL) is stirred at r.t. for 3 days. The insoluble material is filtered off and the solvent is removed. The residue is purified by silica gel chromatography (DCM/methanol 9/1). The solvent is removed. The residue is taken up in DCM. TFA (2 mL) is added. After stirring for 2 hours the solvent is removed.

$C_{12}H_{25}N_3O_3*2C_2HF_3O_2$

ESI Mass spectrum: m/z=260 [M+H]+

The following compounds are prepared accordingly using the respective amine as indicated. Due to conditions applied, the synthesis may yield a free base, a hydrochloride or dihydrochloride salt, a zwitterion or other salt forms which can be applied equally to the syntheses of example compounds as described above.

| Intermediate | | respective amine | Synthesis comment | ESI Mass spectrum |
|---|---|---|---|---|
| XI.2 | ![structure] | (1-Methyl-[1,4]-diazepane | no purification by chromatography | |
| XI.3 | ![structure] | 1-Methyl-piperazine | | 255 (M + H)+ |

| Intermediate | | respective amine | Synthesis comment | ESI Mass spectrum |
|---|---|---|---|---|
| XI.4 | (structure) | Piperidin-4-ol | no purification by chromatography | 256 (M + H)+ |
| XI.5 | (structure) | Dimethyl-piperidin-4-yl-amine | no purification by chromatography | 283 (M + H)+ |
| XI.6 | (structure) | Thiomorpholine-1,1-dioxide | no purification by chromatography | 290 (M + H)+ |
| XI.7 | (structure) | Morpholine | no purification by chromatography | 242 (M + H)+ |
| XI.8 | (structure) | Trimethylamine (1M in THF) | no purification by chromatography | 214 (M + H)+ |
| XI.9 | (structure) | Thiomorpholine-1-oxide | no purification by chromatography | |

Intermediate XII.1

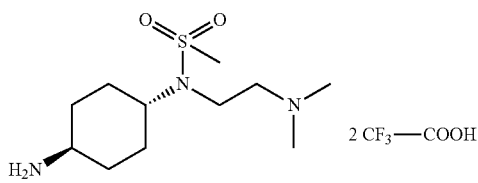

XII.1

Stage 1: A mixture of trans-(4-aminocyclohexyl)-carbamic acid tert-butylester (1.00 g; mmol), (2-bromo-ethyl)-dimethylamine hydrobromide (0.93 g; 3.99 mmol) and DIPEA (1.38 mL; 8.04 mmol) in ACN (16 mL) is stirred at 110° C. for 1 hour in a microwave. The insoluble material is filtered off and the solvent id removed. The residue is stirred in diethyl ether, filtered off and dried.

$C_{15}H_{31}N_3O_2$

ESI Mass spectrum: m/z=286 [M+H]+

Stage 2: A mixture of Intermediate XII.1 stage 1 (200.0 mg; 0.70 mmol) and TEA (97.7 μL; 0.70 mmol) in DCM (10 mL) is stirred at r.t. Methanesulfonyl chloride (54.3 μL; 0.70 mmol) is added drop wise. After stirring at r.t. over night the mixture is washed with water. The organic layer is separated and dried. TFA is added and stirred at r.t. for 1 hour. The solvent is evaporated.

$C_{11}H_{25}N_3O_2S*2C_2HF_3O_2$

The following compounds are prepared accordingly using the respective chloride as indicated. Due to conditions applied, the synthesis may yield a free base, a hydrochloride or dihydrochloride salt, a zwitterion or other salt forms which can be applied equally to the syntheses of example compounds as described above.

| Intermediate | | respective chloride |
|---|---|---|
| XII.2 | (structure) | Acetyl chloride |

Intermediate XIII.1

XIII.1

[Structure of Intermediate XIII.1 with 4 CF₃—COOH]

Stage 1: A mixture of trans-(4-aminocyclohexyl)-carbamic acid tert-butylester (1.00 g; 4.67 mmol) bromo acetic acid methylester (0.88 mL; 9.33 mmol) and DIPEA (1.60 mL; 9.33 mmol) in DCM (50 mL) is stirred at r.t. over night. Another portion of bromo acetic acid methylester (440 µL) and DIPEA (0.8 mL) is added. After stirring for 15 hours the solvent is removed and the residue is purified by RP HPLC (modifier: TFA).

$C_{17}H_{30}N_2O_6$

ESI Mass spectrum: m/z=359 [M+H]+

Stage 2: A mixture of intermediate XIV.1 stage 1 (1.36 g; 3.79 mmol) and aqueous NaOH (1M; 7.60 mL; 7.60 mmol) in methanol (15 mL) is stirred at r.t. over night. Aqueous HCl (1M; 7.60 mL; 7.60 mmol) is added and the organic solvent is removed. The resulting precipitate is filtered off and dried.

$C_{15}H_{26}N_2O_6$

ESI Mass spectrum: m/z=331 [M+H]+

Stage 3: A mixture of intermediate XIII.1 stage 2 (300.0 mg; 0.91 mmol), dimethylpiperidin-4-yl-amine (291.4 µL; 2.00 mmol), HATU (759.6 mg; 2.00 mmol) and DIPEA (0.34 mL; 2.00 mmol) in DMF (6 mL) is stirred at r.t. for 3 days. The mixture is poured in water and extracted with DCM. The organic layer is separated, dried and the solvent is removed. The residue is purified by RP HPLC (modifier: TFA).

$C_{24}H_{46}N_6O_2 * 4 C_2HF_3O_2$

ESI Mass spectrum: m/z=451 [M+H]+

The following compounds are prepared accordingly using the respective amine as indicated. Due to conditions applied, the synthesis may yield a free base, a hydrochloride or dihydrochloride salt, a zwitterion or other salt forms which can be applied equally to the syntheses of example compounds as described above.

| Intermediate | | respective amine | Synthesis comment |
|---|---|---|---|
| XIII.2 | 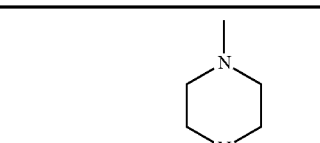 | 1-methyl-piperazine | The resulting amine is filtered through a PL-HCO₃— cartridge to yield the base |

Intermediate XIV.1

XIV.1

[Structure of Intermediate XIV.1 with 3 CF₃—COOH]

Intermediate XII.1 stage 1 (200.0 mg; 0.70 mmol) and TFA (20% in DCM; 5 mL) are stirred at r.t. for 1 hour. The solvent is removed and the residue is further used as crude product.

$C_{10}H_{23}N_3 * 3 C_2HF_3O_2$

Intermediate XV.1

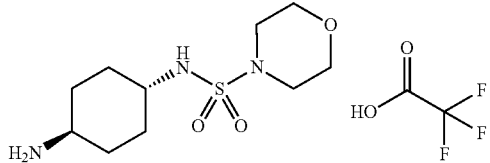

Stage 1: Morpholine (0.50 mL; 5.74 mmol) and sulfuryl chloride (1.50 mL; 18.50 mmol) in ACN (5 mL) are stirred at reflux for 24 hours. The solvent is removed and the residue is taken up in toluene, treated with activated charcoal and filtered off. The solvent is removed.

$C_4H_8ClNO_3S$

Stage 2: A mixture of Intermediate XV.1 stage 1 (173.2 mg; 0.93 mmol) and trans-(4-aminocyclohexyl)-carbamic acid tert-butylester (200.0 mg; 0.93 mmol) and DIPEA (171.2 µL; 1.00 mmol) in ACN (5 mL) is stirred at reflux for 8 hours. The solvent is removed. The residue is taken up in DCM and washed with water. The organic layer is separated and evaporated. The residue is taken up in TFA (3 mL) and stirred at r.t. for 2 hours. The solvent is removed.

$C_{10}H_{21}N_3O_3S*C_2HF_3O_2$

Intermediate XVI.1

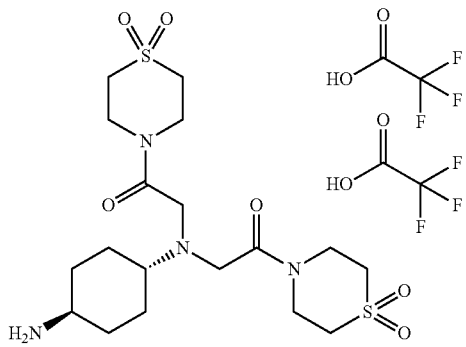

Stage 1: Thiomorpholine-1,1-dioxide (3.00 g; 22.19 mmol) and DIPEA (3.80 mL; 22.19 mmol) in DCM (30 mL) is cooled in an ice bath. Chloro acetylchloride (1.77 mL; 22.19 mmol) is added drop wise. The mixture is stirred at r.t. for 3 hours. The organic solvent is washed with water. The organic layer is separated dried and the solvent is removed.

$C_6H_{10}ClNO_3S$

ESI Mass spectrum: m/z=212 [M+H]+

Stage 2: A mixture of intermediate XVI.1 stage 1 (304.7 mg; 1.42 mmol), trans-(4-aminocyclohexyl)-carbamic acid tert-butylester (300.0 mg; 1.42 mmol) and potassium carbonate (597.6 mg; 4.32 mmol) in acetone (10 mL) is stirred at r.t. over night. The insoluble material is filtered off and the solvent is removed. The residue is purified by silica gel chromatography (DCM/methanol 9/1).

Two products are obtained.

Stage 2A: diacylated product:
Yield: 150.0 mg (19% of theory)
$C_{23}H_{40}N_4O_8S_2$
ESI Mass spectrum: m/z=565 [M+H]+

Stage 2B: monoacylated product:
Yield: 100.0 mg (18% of theory)
$C_{17}H_{31}N_3O_5S$
ESI Mass spectrum: m/z=390 [M+H]+

Stage 3: Intermediate XVI.1 stage 2A (150.0 mg; 0.27 mmol) and TFA (20% in DCM; 5 mL) are stirred at r.t. for 1 hour. The solvent is evaporated.
$C_{18}H_{32}N_4O_6S_2*2C_2HF_3O_2$ Intermediate XVII.1

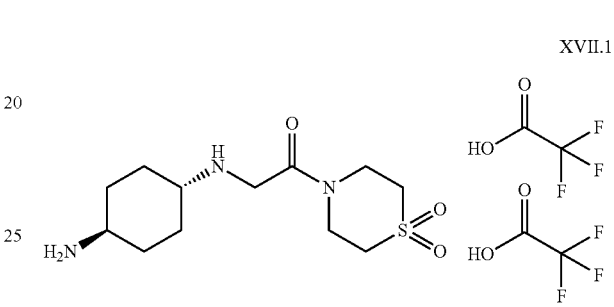

Intermediate XVI.1 stage 2B (100.0 mg; 0.26 mmol) and TFA (20% in DCM; 5 mL) are stirred at r.t. for 1 hour. The solvent is evaporated.
$C_{12}H_{23}N_3O_3S*2C_2HF_3O_2$ Intermediate XVIII.1

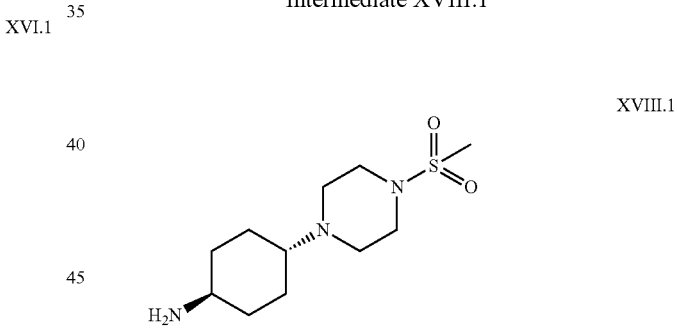

Stage 1: A mixture of 4-(dibenzylamino) cyclohexanone (14.0 g; 47.72 mmol), 1-methylsulphonylpiperazine (8.50 g; 51.76 mmol) and sodium triacetoxy borohydride (17.50 g; 78.44 mmol) in DCM (250 mL) is stirred at r.t. for 4 hours. The mixture is diluted with water (200 mL) and potassium carbonate (20 g). The organic layer is separated, dried and the solvent is removed. The residue is purified by silica gel chromatography (ethyl acetate/methanol 9/1+1%>$NH_3$). The residue is stirred in diethyl ether and filtered off. The resulting cis-product was not isolated.

$C_{25}H_{35}N_3O_2S$
ESI Mass spectrum: m/z=442 [M+H]+

Stage 2: Intermediate XVIII.1 stage 1 (4.75 g; 10.76 mmol) and palladium on charcoal (10%; 2.00 g) in methanol (100 mL) are hydrogenated in a Parr apparatus (50° C.; 50 psi). The catalyst is filtered off and the solvent is removed. The residue is stirred in diethyl ether and filtered off.

$C_{11}H_{23}N_3O_2S$
ESI Mass spectrum: m/z=262 [M+H]+

Intermediate XIX.1

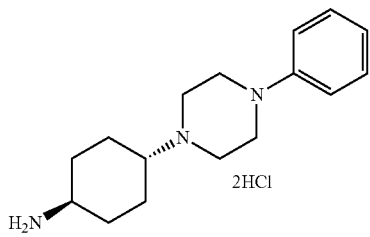

Stage 1: A mixture of 4-(dibenzylamino) cyclohexanone (29.3 g; 99.86 mmol), 1-phenylpiperazine (20.30 g; 125.12 mmol) and methanesulfonic acid (0.10 mL) in toluene (200 mL) is stirred at r.t. for 4 hours with Dean-Stark-apparatus. The resulting precipitate is filtered off and washed with toluene and ethanol. The solvent is evaporated. The residue is recrystallized from methanol.
Combined yield: 37.50 g (86% of theory)
$C_{30}H_{35}N_3$ Stage 2: Intermediate XIX.1 stage 1 (36.50 g; 83.40 mmol) is diluted in THF (400 mL) and ethanol (400 mL). NaBH$_4$ (8.00 g; 0.21 mmol) is added portion by portion. The mixture is stirred at reflux for 8 hours. THF is removed and the mixture is diluted with water (2 L). The resulting precipitate is filtered off and washed with water and ethanol. The residue is taken up in methanol (200 mL) and HCl (36%) is added till a pH of 2 is reached. The mixture is stirred in an ice bath for 30 minutes. The precipitate is filtered off and washed with methanol and diethyl ether.
$C_{30}H_{37}N_3*2HCl$ Stage 3: Intermediate XIX.1 stage 2 (21.60 g; 42.14 mmol) and palladium on charcoal (10%; 5.00 g) in methanol (500 mL) are hydrogenated in a Parr apparatus (50° C.; 50 psi). The catalyst is filtered off and the solvent is removed. The residue is crystallized from ethanol, filtered off and washed with ethanol and diethyl ether.
C16H25N3*2HCl
ESI Mass spectrum: m/z=260 [M+H]+

Intermediate XX.1

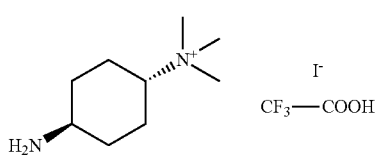

Stage 1: A mixture of trans-(4-aminocyclohexyl)-carbamic acid tert-butylester (200.0 mg; 0.93 mmol), methyl iodide (200.0 µL; 3.21 mmol) and potassium carbonate (445.0 mg; 3.22 mmol) in acetone (6 mL) and methanol (4 mL) is stirred at 50° C. for 10 minutes and then at r.t. over night. The insoluble material is filtered off and the solvent is removed.
$C_{14}H_{29}N_2O_2*I$
ESI Mass spectrum: m/z=257 [M+]

Stage 2: Intermediate XX.1 stage 1 (400.0 mg) and TFA (20% in DCM; 5 mL) are stirred at r.t. for 1 hour. The solvent is evaporated and the residue is further used as crude product.
$C_9H_{21}N_2*I*C_2HF_3O_2$ Intermediate XXI.1

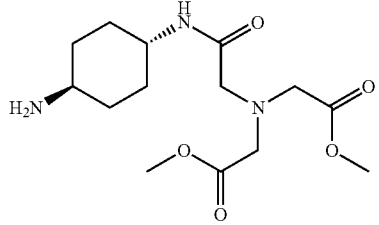

Stage 1: A mixture of trans-(4-aminocyclohexyl)-carbamic acid tert-butylester (2.00 g; 9.33 mmol) and DIPEA (1.55 mL; 9.33 mmol) in DCM (20 mL) is cooled in an ice bath. Bromo-acetyl bromide (0.81 mL; 9.33 mmol) is added drop wise. The mixture is stirred at r.t. for 2 hours. The organic layer is washed with water, separated, dried and evaporated. The residue is stirred in diethyl ether, filtered off and dried.
$C_{13}H_{23}BrN_2O_3$
ESI Mass spectrum: m/z=333 [M–H]–

Stage 2: A mixture of Intermediate XXI.1 stage 1 (440.0 mg; 1.31 mmol) and (methoxycarbonylmethyl-amino)-acetic acid methyl ester hydrochloride (259.4 mg; 1.31 mmol), potassium iodide (21.8 mg; 0.13 mmol) and DIPEA (449.4 µL; 2.63 mmol) in DMF (2 mL) is stirred at 50° C. over night. The insoluble material is filtered off. The mother liquor is purified by RP HPLC (modifier: TFA).
$C_{19}H_{33}N_3O_7$
ESI Mass spectrum: m/z=416 [M+H]+

Stage 3: Intermediate XXI.1 stage 2 (370.0 mg; 0.89 mmol) and TFA (20% in DCM; 10 mL) are stirred at r.t. for 2 hours. The solvent is removed. The residue is taken up in methanolic HCl and evaporated.
$C_{14}H_{25}N_3O_5*2HCl$
ESI Mass spectrum: m/z=316 [M+H]+

Intermediate XXII.1

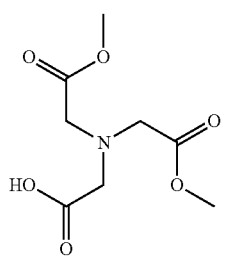

A mixture of bromo acetic acid (351.5 mg; 2.53 mmol), (methoxycarbonylmethyl-amino)acetic acid methyl ester hydrochloride (500.0 mg; 2.53 mmol), potassium carbonate (1.04 g; 7.50 mmol) and potassium iodide (50.0 mg; 0.30 mmol) in acetone (10 mL) is stirred at r.t. for 3 days. The insoluble material is filtered off and discarded. The solvent is evaporated.
$C_8H_{13}NO_6$

47

Intermediate XXIII.1

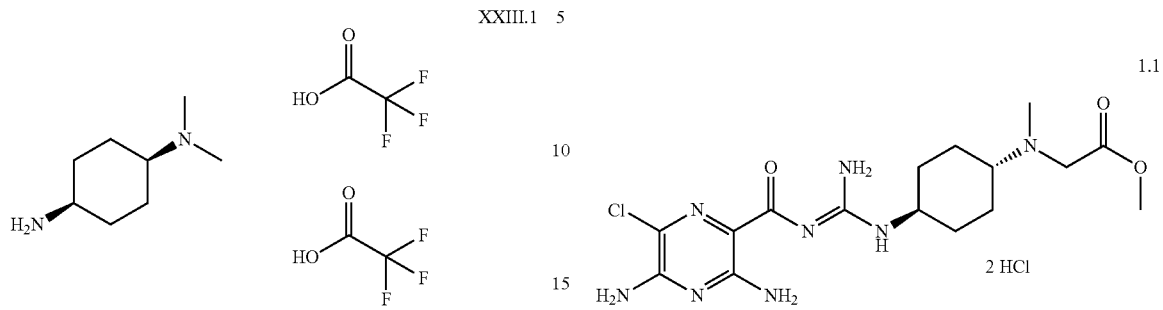

A mixture of cis-(4-aminocyclohexyl)-carbamic acid tert-butylester (320.0 mg; 1.49 mmol) and formaldehyde (37% in water; 160.0 µL; 2.14 mmol) in methanol (5 mL) is stirred at r.t. for 15 minutes. NaBH$_4$ (53.8 mg; 2.24 mmol) is added. After 30 minutes of stirring further formaldehyde (160.0 µL) is added and stirred for another 20 minutes. NaBH$_4$ (53.8 mg) is added and the mixture is stirred at r.t. over night. The solvent is evaporated. The residue is taken up in DCM/methanol (19/1) and washed with NaOH (1M). The organic layer is separated, dried and the solvent is removed. The residue is taken up in DCM and TFA (25% in DCM). After 4 hours of stiffing at r.t. the solvent is evaporated.

$C_8H_{18}N_2 * 2C_2HF_3O_2$

48

SYNTHESIS OF EXAMPLES

Example 1.1

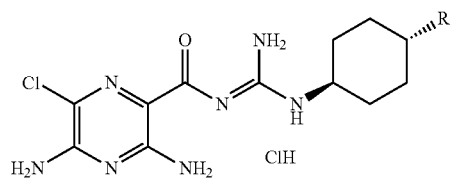

A mixture of intermediate C.1 (70.0 mg; 0.27 mmol) and intermediate 1.1 (98.5 mg; 0.23 mmol) in THF (2 mL) is stirred at 70° C. for 3 days. The solvent is removed and the residue is purified by RP HPLC (modifier: TFA). The residue is taken up in methanolic HCL and the solvent is evaporated.

$C_{16}H_{25}ClN_8O_3 * 2HCl$

ESI Mass spectrum: m/z=413 [M+H]+

HPLC analytics: RT=0.69 min (HPLC method A)

The following compounds of Table I are prepared accordingly using the respective amine and the respective thiourea as indicated. Due to conditions applied, the synthesis may yield a free base, a hydrochloride or dihydrochloride salt, a zwitterion or other salt forms which can be applied equally to the syntheses of example compounds as described above.

TABLE 1

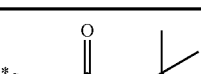

| Example | R | respective amine | Synthesis comment | ESI Mass spectrum | HPLC Retention time (min) | HPLC method |
|---|---|---|---|---|---|---|
| 1.2 | 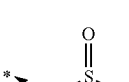 | (4-amino-cyclohexyl)-carbamic acid tert-butylester | Purification by RP HPLC (modifier: NH$_3$) | 427 (M + H)+ | 1.08 | A |
| 1.3 | 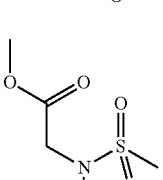 | Intermediate II.1 | | 405 (M + H)+ | 0.86 | A |
| 1.4 |  | Intermediate III.1 | | 477 (M + H)+ | 0.94 | A |

TABLE 1-continued

| Example | R | respective amine | Synthesis comment | ESI Mass spectrum | HPLC Retention time (min) | HPLC method |
|---|---|---|---|---|---|---|
| 1.5 | *-HN-CH2-C(=O)-O-CH3 | Intermediate I.2 | | 399 (M + H)+ | 0.69 | A |
| 1.6 | N-methyl-N-benzyl | Intermediate I.3 | | 431 (M + H)+ | 0.84 | A |
| 1.7 | N(CH2C(=O)OBn)(CH2C(=O)OMe) | Intermediate IV.1a | | 547 (M + H)+ | 1.17 | A |
| 1.8 | N(CH2C(=O)OMe)2 | Intermediate IV.1b | | 471 (M + H)+ | 0.91 | A |
| 1.9 | N(CH2C(=O)-N-methylpiperazine)(CH2C(=O)OMe) | Intermediate V.1 | | 539 (M + H)+ | 0.71 | A |
| 1.10 | N(CH2C(=O)-4-methylpiperidine)(CH2C(=O)OMe) | Intermediate V.2 | | 538 (M + H)+ | 0.95 | A |

TABLE 1-continued

[Structure: Cl-substituted pyrazine carboxamide with diamino groups, linked via guanidine to trans-cyclohexyl-R, as ClH salt]

| Example | R | respective amine | Synthesis comment | ESI Mass spectrum | HPLC Retention time (min) | HPLC method |
|---|---|---|---|---|---|---|
| 1.11 | [thiomorpholine dioxide-CH2-C(O)-N(*)-CH2-C(O)OMe] | Intermediate V.3 | | 574 (M + H)+ | 0.77 | A |
| 1.12 | [N-methyl-N-(2-fluorobenzyl), *] | Intermediate VI.2 | | 449 (M + H)+ | 0.87 | A |
| 1.13 | [N-methyl-N-(4-fluorobenzyl), *] | Intermediate VI.1 | | 449 (M + H)+ | 1.25 | B |
| 1.14 | [*-NHC(O)CH2-N+(Me)(piperazine-N-Me), Cl−] | Intermediate VII.1 | | 481 M+ | 0.50 | C |
| 1.15 | [N,N-dimethylamino, *] | 4-Dimethyl-amino cyclohexyl amin | | 355 (M + H)+ | 0.68 | A |
| 1.16 | [*-NH-C(O)-O-tBu] (cis) | 1-N-Boc-cis-1,4-cyclohexyl-diamine | | 427 (M + H)+ | 1.16 | A |
| 1.17 | [*-NH2] (cis) | 1-N-Boc-cis-1,4-cyclohexyl-diamine | Deprotection of the amine by TFA (25% in DCM) | 327 (M + H)+ | 0.64 | A |

TABLE 1-continued

| Example | R | respective amine | Synthesis comment | ESI Mass spectrum | HPLC Retention time (min) | HPLC method |
|---|---|---|---|---|---|---|
| 1.18 | | (4-amino-cyclohexyl)-carbamic acid benzyl ester | | 461 (M + H)+ | 1.55 | D |
| 1.19 | | Intermediate VIII.1 | Purification by RP HPLC (modifier: NH$_3$) | 412 (M + H)+ | 1.40 | D |
| 1.20 | | Intermediate VIII.2 | Purification by RP HPLC (modifier: NH$_3$) | 452 (M + H)+ | 1.08 | D |
| 1.21 | | Intermediate IX.1 | | 369 (M + H)+ | 1.17 | A |
| 1.22 | | Intermediate IX.2 | | 411 (M + H)+ | 1.06 | A |
| 1.23 | | Intermediate X.1 | | 412 (M + H)+ | 0.75 | A |
| 1.24 | | 4-morpholin-4-yl-cyclohexyl-amine | | 397 (M + H)+ | 1.67 | A |
| 1.25 | | 4-(4-methyl-piperazin-1-yl)-cyclohexyl-amine | | 410 (M + H)+ | 0.64 | A |

TABLE 1-continued

| Example | R | respective amine | Synthesis comment | ESI Mass spectrum | HPLC Retention time (min) | HPLC method |
|---|---|---|---|---|---|---|
| 1.26 | | Intermediate XI.1 | | 472 (M + H)+ | 0.49 | F |
| 1.27 | | Intermediate XI.2 | | 481 (M + H)+ | 0.48 | G |
| 1.28 | | Intermediate XI.3 | | 467 (M + H)+ | 0.74 + 0.76 | A |
| 1.29 | | Intermediate XII.1 | | 476 (M + H)+ | 0.52 | G |
| 1.30 | | Intermediate XII.2 | | 440 (M + H)+ | 0.53 | G |
| 1.31 | | Intermediate XIII.1 | Purification by RP HPLC (modifier: NH₃) | 663 (M + H)+ | 0.66 | F |
| 1.32 | | Intermediate XIII.2 | Purification by RP HPLC (modifier: NH₃) | 607 (M + H)+ | 0.58 | F |

TABLE 1-continued

| Example | R | respective amine | Synthesis comment | ESI Mass spectrum | HPLC Retention time (min) | HPLC method |
|---|---|---|---|---|---|---|
| 1.33 | *HN-CH2CH2-N(CH3)2 | Intermediate XIV.1 | Purification by RP HPLC (modifier: NH3) | 398 (M + H)+ | 0.61 | F |
| 1.34 | *HN-SO2-morpholine | Intermediate XV.1 | | 476 (M + H)+ | 0.96 | A |
| 1.35 | bis(thiomorpholine dioxide) acetyl N | Intermediate XVI.1 | Purification by RP HPLC (modifier: NH3) | 677 (M + H)+ | 0.51 | G |
| 1.36 | *HN-CO-CH2-thiomorpholine dioxide | Intermediate XVII.1 | | 502 (M + H)+ | 0.55 | F |
| 1.37 | *N-piperazine-SO2CH3 | Intermediate XVIII.1 | | 474 (M + H)+ | 0.7 | A |
| 1.38 | *N-piperazine-phenyl | Intermediate XIX.1 | | 472 (M + H)+ | 0.89 | A |
| 1.39 | *N+(CH3)3 Cl- | Intermediate XX.1 | | 369 (M+) | 0.64 | A |
| 1.40 | *HN-CO-CH2-(4-hydroxypiperidine) | Intermediate XI.4 | | 468 (M + H)+ | 0.75 | A |

TABLE 1-continued

| Example | R | respective amine | Synthesis comment | ESI Mass spectrum | HPLC Retention time (min) | HPLC method |
|---|---|---|---|---|---|---|
| 1.41 | (piperidine-N,N-dimethylamino acetamide) | Intermediate XI.5 | | 495 (M + H)+ | 0.70 | A |
| 1.42 | (thiomorpholine-1,1-dioxide acetamide) | Intermediate XI.6 | | 502 (M + H)+ | 0.87 | A |
| 1.43 | (morpholine acetamide) | Intermediate XI.7 | | 454 (M + H)+ | 0.76 | A |
| 1.44 | (trimethylammonium acetamide) | Intermediate XI.8 | | 426 (M+) | 0.77 | A |
| 1.45 | (thiomorpholine-1-oxide acetamide) | Intermediate XI.9 | | 486 (M + H)+ | 0.75 | A |
| 1.46 | (iminodiacetic acid dimethyl ester acetamide) | Intermediate XXI.1 | | 528 (M + H)+ | 0.62 | G |
| 1.47 | N,N-dimethylamino (cis) | Intermediate XXIII.1 | | 355 (M + H)+ | 0.65 | A |

Example 2.1

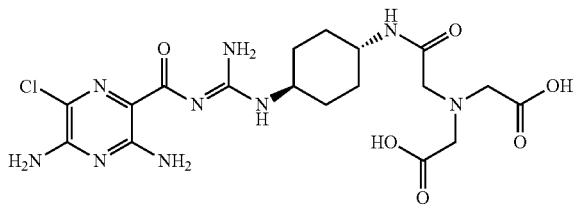

A mixture of example 1.46 (75.0 mg; 0.14 mmol) and NaOH (1M; 0.28 mL; 0.28 mmol) in methanol (6 mL) is stirred at 50° C. for 5 hours and at r.t. over night. The solvent is removed. The residue is purified by RP HPLC (modifier: TFA).

Yield: 9.0 mg (13% of theory)
$C_{18}H_{26}ClN_9O_6$
ESI Mass spectrum: m/z=500 [M+H]+
HPLC analytics: RT=0.56 min (HPLC method G)

The following compounds of Table 2 are prepared accordingly using the respective ester as indicated. Due to conditions applied, the synthesis may yield a free base, a hydrochloride or dihydrochloride salt, a zwitterion or other salt forms which can be applied equally to the syntheses of example compounds as described above.

TABLE 2

| Example | R | Respective ester | Synthesis comment | ESI Mass spectrum | HPLC Retention time (min) | HPLC method |
|---|---|---|---|---|---|---|
| 2.2 | (4-carboxybenzamide) | Example 5.1 | Use of TFA (20% in DCM) for hydrolysis | 475 (M + H)+ | 1.07 | A |
| 2.3 | (thiomorpholine-1,1-dioxide acetyl glycine) | Example 1.11 | | 560 (M + H)+ | 0.70 | A |
| 2.4 | (4-methylpiperazine acetyl glycine) | Example 1.9 | | 525 (M + H)+ | 0.61 | A |

TABLE 2-continued

[Structure: chloropyrazine diamine carboxamide guanidine cyclohexyl-R]

| Example | R | Respective ester | Synthesis comment | ESI Mass spectrum | HPLC Retention time (min) | HPLC method |
|---|---|---|---|---|---|---|
| 2.5 | [4-methylpiperidine-acetyl-N-CH2-COOH] | Example 1.10 | | 524 (M + H)+ | 0.93 | A |
| 2.6 | [methanesulfonyl-N-CH2-COOH] | Example 1.4 | | 463 (M + H)+ | 0.67 | G |
| 2.7 | [H2N-CH2-COOH] | Example 1.5 | | 385 (M + H)+ | 0.66 | G |
| 2.8 | [CH3-NH-CH2-COOH] | Example 1.1 | | 399 (M + H)+ | 0.42 | A |

Example 3.1

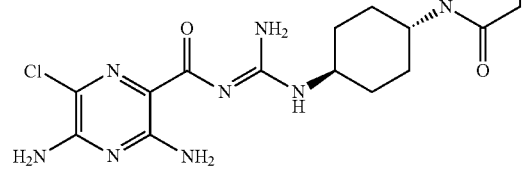

3.1

A mixture of Example 1.28 (70.0 mg; 0.12 mmol), methyl iodide (7.5 µL; 0.12 mmol) and DIPEA (62.1 µL; 0.36 mmol) in acetone (6 mL) is stirred at r.t. over night. The resulting precipitate is filtered off and washed with diethyl ether.

Yield: 28.0 mg (38% of theory)

$C_{20}H_{34}ClN_{10}O_2*I$

ESI Mass spectrum: m/z=481 [M+]

HPLC analytics: RT=0.76 min (HPLC method A)

The following compounds of Table 3 are prepared accordingly using the respective amine as indicated. Due to conditions applied, the synthesis may yield a free base, a hydrochloride or dihydrochloride salt, a zwitterion or other salt forms which can be applied equally to the syntheses of example compounds as described above.

TABLE 3

[Structure: 6-chloro-3,5-diamino-pyrazine-2-carboxamide core with acylguanidine linked to trans-4-R-cyclohexyl group]

| Example | R | Respective amine | Synthesis comment | ESI Mass spectrum | HPLC Retention time (min) | HPLC method |
|---|---|---|---|---|---|---|
| 3.2 | [trimethylammonium-piperidine linked via acetyl-N-acetyl-piperidinyl-trimethylammonium, 2 I⁻] | Example 1.31 | No use of DIPEA; purification by RT HPLC (modifier: TFA) | 346 (M + H)++ | 0.49 | G |
| 3.3 | [dimethyl-piperazinium linked via acetyl-N-acetyl-piperazinium-dimethyl, 2 I⁻] | Example 1.32 | No use of DIPEA; purification by RP HPLC (modifier: TFA) | 318 (M + H)++ | 0.44 | G |
| 3.4 | [acetamide-diazepane-dimethylammonium I⁻] | Example 1.27 | No use of DIPEA | 496 (M + H)+ | 0.51 | G |

Example 4.1

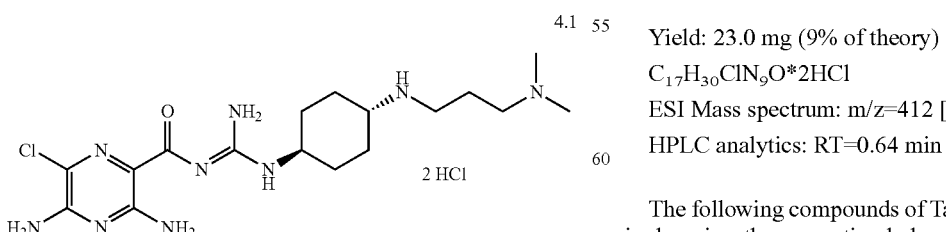

4.1

A mixture of Example 6.2 (300.0 mg; 0.54 mmol), (3-chloro-propyl)-dimethyl-amine hydrochloride (85.5 mg; 0.54 mmol) and potassium carbonate (224.2 mg; 1.62 mmol) in DMF (5 mL) is stirred at r.t. over night. The insoluble material is filtered off and the solvent is removed. The residue is purified by RP HPLC (modifier: TFA).

Yield: 23.0 mg (9% of theory)

$C_{17}H_{30}ClN_9O*2HCl$

ESI Mass spectrum: m/z=412 [M+H]+

HPLC analytics: RT=0.64 min (HPLC method F)

The following compounds of Table 4 are prepared accordingly using the respective halogenide as indicated. Due to conditions applied, the synthesis may yield a free base, a hydrochloride or dihydrochloride salt, a zwitterion or other salt forms which can be applied equally to the syntheses of example compounds as described above.

TABLE 4

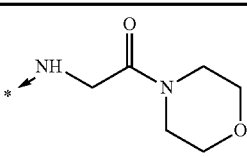

| Example | R | Respective halogenide | Synthesis comment | ESI Mass spectrum | HPLC Retention | HPLC method |
|---------|---|----------------------|-------------------|-------------------|----------------|-------------|
| 4.2 | 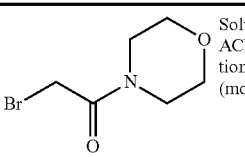 | 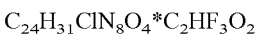 | Solvent used is ACN; purification by RP HPLC (modifier: NH₃) | 454 (M + H)+ | 0.54 | F |

Example 5.1

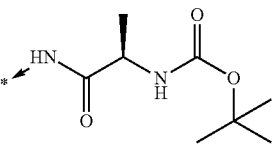

5.1

A mixture of terephalic acid mono tert-butylester (60.0 mg; 0.27 mmol), HATU (90.0 mg; 02.4 mmol) and TEA (130.0 µL; 0.94 mmol) in DMF (1 mL) is stirred at r.t. for 20 minutes. Example 6.2 (110.0 mg; 0.20 mmol) is added. After stiffing at r.t. over night the mixture is purified by RP HPLC (Modifier: TFA).

Yield: 57.0 mg (45% of theory)

$C_{24}H_{31}ClN_8O_4 * C_2HF_3O_2$

ESI Mass spectrum: m/z=531 [M+H]+

HPLC analytics: RT=1.29 min (HPLC method A)

The following compounds of Table 5 are prepared accordingly using the respective amine and the respective acid as indicated. Due to conditions applied, the synthesis may yield a free base, a hydrochloride or dihydrochloride salt, a zwitterion or other salt forms which can be applied equally to the syntheses of example compounds as described above.

TABLE 5

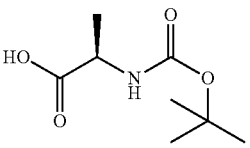

| Example | R | Respective amine | Respective acid | Synthesis comment | ESI Mass spectrum | HPLC Retention time (min) | HPLC method |
|---------|---|------------------|-----------------|-------------------|-------------------|---------------------------|-------------|
| 5.2 | 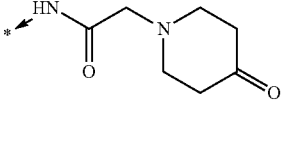 | Example 6.2 | 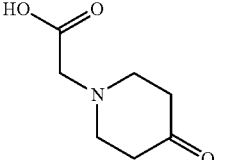 | Use of DIPEA, instead of TEA | 498 (M + H)+ | 0.67 | G |
| 5.3 |  | Example 6.2 |  | Use of DIPEA, instead of TEA; purification by RP HPLC (modifier: NH₃) | 466 (M + H)+ | 0.55 | F |

TABLE 5-continued

| Example | R | Respective amine | Respective acid | Synthesis comment | ESI Mass spectrum | HPLC Retention time (min) | HPLC method |
|---|---|---|---|---|---|---|---|
| 5.4 | | Example 6.2 | Intermediate XXV.1/HATU (Side reaction with HATU) | Use of DIPEA, instead of TEA | 425 (M+) | 0.52 | G |
| 5.5 | | 1-Methyl-piperazine | Example 2.7 | Use of DIPEA, instead of TEA; use of TBTU instead of HATU | 467 (M + H)+ | 0.55 | F |

Example 6.1

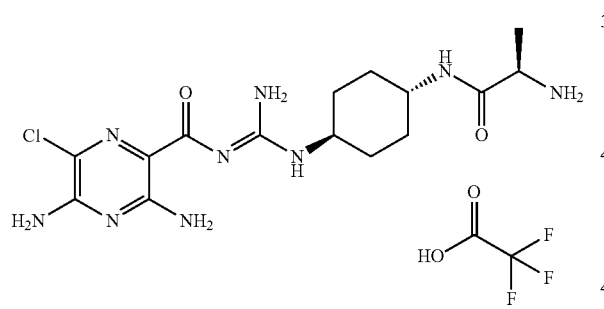

A mixture of Example 5.2 (14.0 mg; 0.03 mmol) and TFA (10% in DCM; 3 mL) is stirred at r.t. over night. The solvent is removed.

The following compounds of Table 6 are prepared accordingly using the respective protected amine as indicated. Due to conditions applied, the synthesis may yield a free base, a hydrochloride or dihydrochloride salt, a zwitterion or other salt forms which can be applied equally to the syntheses of example compounds as described above.

TABLE 6

| Example | R | Respective protected amine | Synthesis comment | ESI Mass spectrum | HPLC Retention time (min) | HPLC method |
|---|---|---|---|---|---|---|
| 6.2 | NH2 | Example 1.2 | The residue is stirred in diethyl ether, filtered off, dried. Taken-up in methanolic HCl and the solvent is removed | 327 = (M + H)+ | 0.46 | G |

Yield: 15.0 mg (100% of theory)
$C_{15}H_{24}ClN_9O_2 \cdot C_2HF_3O_2$
ESI Mass spectrum: m/z=398 [M+H]+
HPLC analytics: RT=0.51 min (HPLC method G)

Example 7

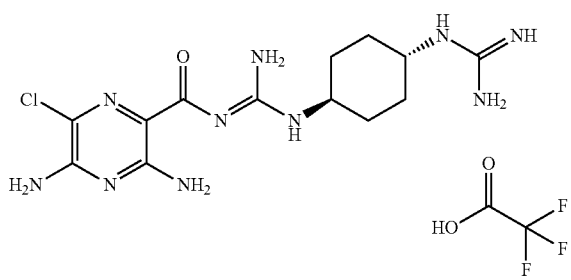

A mixture of example 6.2 (70.0 mg; 0.16 mmol), 1H-1,2,4-triazole-1-carboxamidine hydrochloride (23.6 mg; 0.16 mmol) and DIPEA (20.7 mg; 0.16 mmol) in ethanol (3 mL) is stirred at 70° C. for 3 hours. The mixture is purified by RP HPLC (modifier: TFA). The residue is taken up in diethyl ether and the solvent is removed.
Yield: 26.0 mg (34% of theory)
$C_{13}H_{21}ClN_{10}O \cdot C_2HF_3O_2$
ESI Mass spectrum: m/z=369 [M+H]+
HPLC analytics: RT=0.77 min (HPLC method A)

Example 8

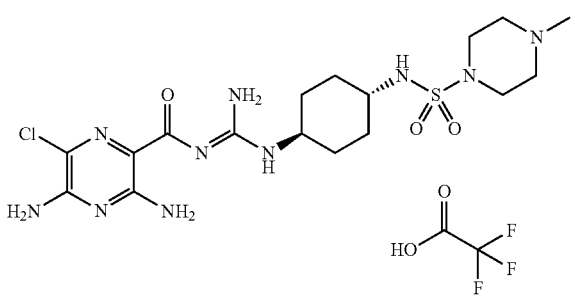

A mixture of Example 6.2 (160.0 mg; 0.36 mmol), 4-methyl-piperazine-1-sulfonyl chloride hydrochloride (120.0 mg; 0.51 mmol) and DABCO (diazabicyclo-octan; 220.0 mg; 1.96 mmol) in DCM (5 mL) is stirred at r.t. over night. The insoluble material is filtered off and the solvent is removed. The residue is purified by RP HPLC (modifier: TFA). The residue is taken up in diethyl ether, filtered off and dried.
Yield: 27.0 mg (12% of theory)
$C_{17}H_{29}ClN_{10}O_3S \cdot C_2HF_3O_2$
ESI Mass spectrum: m/z=489 [M+H]+
HPLC analytics: RT=0.52 min (HPLC method G)

Analytical Methods and Preparative Chromatography

As a rule, $^1$H-NMR and mass spectra have been obtained for the compounds prepared. Mass peaks given (e.g. (M+H)+; (M+HCOO)—) refer to monoisotopic molecular weight. $R_f$ values from TLC are determined using ready-made silica gel 60 TLC plates $F_{254}$ (E. Merck, Darmstadt, Item no. 1.05714) without chamber saturation or using ready-made aluminium oxide 60 $F_{254}$ TLC plates (E. Merck, Darmstadt, Item no. 1.05713) without chamber saturation. The ration given for the eluents relate to units by volume of the solvent in question. The units by volume for $NH_3$ relate to a concentrated solution of $NH_3$ in water. For silica gel chromatographic purifications, silica gel made by Millipore (MATREX™, 35-70 my) is used.

Analytical HPLC/MS Methods

The HPLC retention times given are measured under the following parameters. Unless a temperature value is given, the system is run at r.t.

HPLC Method A

| Column | | SunFire C18 3 × 30 mm, 2.5 μm (Waters) | | |
|---|---|---|---|---|
| Gradient time [min] | % Sol [$H_2O$, 0.1% TFA] | % Sol [methanol] | Flow [mL/min] | Temp [° C.] |
| 0.00 | 95 | 5 | 1.8 | 60 |
| 0.25 | 95 | 5 | 1.8 | 60 |
| 1.70 | 0 | 100 | 1.8 | 60 |
| 1.75 | 0 | 100 | 2.5 | 60 |
| 1.90 | 0 | 100 | 2.5 | 60 |

HPLC Method B

| Column | | XBridge C18 4.6 × 30 mm, 2.5 μm (Waters) | | |
|---|---|---|---|---|
| Gradient time [min] | % Sol [$H_2O$, 0.1% TFA] | % Sol [methanol] | Flow [mL/min] | Temp [° C.] |
| 0.00 | 95 | 5 | 4.0 | 60 |
| 0.05 | 95 | 5 | 3.0 | 60 |
| 2.05 | 0 | 100 | 3.0 | 60 |
| 2.10 | 0 | 100 | 4.5 | 60 |
| 2.40 | 0 | 100 | 4.5 | 60 |

HPLC Method C

| Column | | XBridge C18 3 × 30 mm, 2.5 μm (Waters) | | |
|---|---|---|---|---|
| Gradient time [min] | % Sol [$H_2O$, 0.1% TFA] | % Sol [methanol] | Flow [mL/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3.0 | 60 |
| 1.40 | 0 | 100 | 3.0 | 60 |

HPLC Method D

| Column | | SunFire C18 4.6 × 30 mm, 2.5 μm (Waters) | | |
|---|---|---|---|---|
| Gradient time [min] | % Sol [$H_2O$, 0.1% TFA] | % Sol [methanol] | Flow [mL/min] | Temp [° C.] |
| 0.00 | 95 | 5 | 4.0 | 60 |
| 0.05 | 95 | 5 | 3.0 | 60 |
| 2.05 | 0 | 100 | 3.0 | 60 |
| 2.10 | 0 | 100 | 4.5 | 60 |
| 2.40 | 0 | 100 | 4.5 | 60 |

HPLC Method E

| Column | XBridge C18 3 × 30 mm, 2.5 μm (Waters) | | | |
|---|---|---|---|---|
| Gradient time [min] | % Sol [H$_2$O, 0.1% NH$_3$] | % Sol [methanol] | Flow [mL/min] | Temp [° C.] |
| 0.00 | 95 | 5 | 2.2 | 60 |
| 0.30 | 95 | 5 | 2.2 | 60 |
| 1.50 | 0 | 100 | 2.2 | 60 |
| 1.55 | 0 | 100 | 2.9 | 60 |
| 1.70 | 0 | 100 | 2.9 | 60 |

HPLC Method F

| Column | XBridge C18 3 × 30 mm, 2.5 μm (Waters) | | | |
|---|---|---|---|---|
| Gradient time [min] | % Sol [H$_2$O, 0.1% NH$_3$] | % Sol [acetonitrile] | Flow [mL/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3.0 | 60 |
| 1.40 | 0 | 100 | 3.0 | 60 |

HPLC Method G

| Column | SunFire 3 × 30 mm, 2.5 μm (Waters) | | | |
|---|---|---|---|---|
| Gradient time [min] | % Sol [H$_2$O, 0.1% NH$_3$] | % Sol [acetonitrile] | Flow [mL/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3.0 | 60 |
| 1.40 | 0 | 100 | 3.0 | 60 |

HPLC Method H

| Column | XBridge C18 3 × 30 mm, 2.5 μm (Waters) | | | |
|---|---|---|---|---|
| Gradient time [min] | % Sol [H$_2$O, 0.1% NH$_3$] | % Sol [methanol] | Flow [mL/min] | Temp [° C.] |
| 0.00 | 95 | 5 | 2.2 | 60 |
| 0.30 | 95 | 5 | 2.2 | 60 |
| 1.50 | 0 | 100 | 2.2 | 60 |
| 1.55 | 0 | 100 | 2.9 | 60 |
| 1.65 | 0 | 100 | 2.9 | 60 |

Preparative HPLC/MS Methods

The compounds are, if not stated otherwise, purified by RP HPLC.

Columns used are SunFire C18 or XBridge C18 from Waters. Modifiers applied are TFA or NH$_3$ as indicated.

Permeability and Efflux in CALU-3 Cells:

Permeability measurements across polarized, confluent CALU-3 cell monolayers grown on permeable filter supports are used to provide information on the potential of a compound to pass the lung epithelium. Apparent permeability coefficients (Papp) of the compounds across the CALU-3 cell monolayers are measured (pH 7.4, 37° C.) in apical-to-basal (AB) and basal-to-apical (BA) transport direction. AB permeability (Papp, AB) represents drug absorption from the lung lumen into the blood and BA permeability (Papp, BA) drug transport from the blood into the lung lumen mainly via passive permeability since Calu-3 cells as well as lung epithelial cells do not express efflux transporters like P-gp, while uptake transporters may be expressed.

CALU-3 cells (1-2×10$^5$ cells/1 cm$^2$ area) are seeded on filter inserts (Costar transwell polycarbonate filters, 0.4 μm pore size) and cultured (DMEM) for 10-12 days until tight monolayers are formed. Compounds of interest are dissolved in appropriate solvent (DMSO, 10 mM stock solution). Stock solutions are diluted with HTP-4 buffer (128.13 mM NaCl, 5.36 mM KCl, 1 mM MgSO4, 1.8 mM CaCl$_2$, 4.17 mM NaHCO3, 1.19 mM Na2HPO4×7H2O, 0.41 mM NaH2PO4×H2O, 15 mM HEPES, 20 mM glucose, 0.25% BSA, pH 7.4) to prepare the transport solutions (10 μM compound, final DMSO<=0.5%). The transport solution (TL) is applied to the apical or basolateral donor side for measuring A-B or B-A permeability (3 filter replicates), respectively. The receiver side contains the same buffer as the donor side. After 30 min of accommodation, samples are collected at the start t0=0 min and at the end of the experiment tn=90 min from the donor and at 0, 30, 60, and 90 min also from the receiver chamber. Volume removed is replenished by HTP-4 buffer. The compound concentration in the samples is measured by HPLC-MS/MS or scintillation counting. The permeability coefficient (Papp) and efflux ratio are calculated according to:

*Papp* [cm/s]=(concentration receiver [nM]*volume receiver [mL]/time interval [sec])*(1/filter area)*(1/donor concentration [nM])

Efflux ratio or Uptake ratio=*Papp,BA/Papp,AB*

| Example | 1.3 | 1.4 | 1.15 | 1.5 | 1.23 | 3.1 | 1.42 | 1.45 | 1.11 |
|---|---|---|---|---|---|---|---|---|---|
| P BA [cm/sec] | 7.15 E−07 | 4.95 E−07 | <2.73 E−07 | 7.59 E−07 | 1.93 E−07 | 2.29 E−07 | 3.64 E−07 | 5.57 E−07 | 3.81 E−07 |

| Example | 1.9 | 1.13 | 2.2 | 5.2 | 6.1 | 8 | 1.14 | 1.26 | 1.27 |
|---|---|---|---|---|---|---|---|---|---|
| P BA [cm/sec] | 1.02 E−07 | 7.53 E−06 | 2.31 E−07 | 4.21 E−07 | 2.25 E−07 | 3.54 E−07 | 3.16 E−07 | 6.50 E−07 | 5.30 E−07 |

| Example | 1.30 | 1.29 | 1.33 | 1.36 | 1.35 | 4.2 | 5.3 | 5.5 | 5.4 |
|---|---|---|---|---|---|---|---|---|---|
| P BA [cm/sec] | 3.26 E−07 | 5.19 E−07 | <6.30 E−07 | <3.22 E−07 | <9.78 E−08 | 3.14 E−07 | 3.02 E−07 | 2.60 E−07 | 2.13 E−07 |

| Example | 3.4 | 4.1 | 1.32 | 3.3 | 1.31 | 6.2 |
|---|---|---|---|---|---|---|
| P BA [cm/sec] | 1.23 E−07 | <2.72 E−06 | <9.81 E−07 | <3.75 E−06 | 1.35 E−06 | <2.72 E−07 |

The following abbreviations are used above and hereinafter:
ACN Acetonitrile
BOC tert-Butoxycarbonyl
DCM Methylene chloride
DIPEA Diisopropyl-ethylamine
DMF N,N-Dimethylformamide
DPPF 1,1'-Bis(diphenylphosphino)ferrocene
ESI Electrospray ionization
h hour
HATU O-(7-Azabenzotriazol-1-yl)-N,N,N',N'-tetramethyluronium-hexafluorophosphate HCl Hydrochloric acid
LiHMDS Lithium bis(trimethylsilyl)amide
MeOH methanol
Min minutes
Mp melting point
NaOH aqueous sodium hydroxide solution
n.d. not determined
Pd/C palladium on charcoal
r.t. ambient temperature (about 20° C.)
RT retention time
TBME Methyl tert-butyl ether
TBTU 2-(1H-Benzotriazol-1-yl)-1,1,3,3-tetramethyluronium-tetrafluoroborate
TEA Triethylamine
TFA Trifluoroacetic acid
THF Tetrahydrofuran
TMS Trimethylsilyl

arrow and asterisk indicate the binding site, i.e. the point of attachment (here: atom "A") within a chemical entity (here exemplified by the group "A-R")

Pharmacological Test Method:

Other features and advantages of the present invention will become apparent from the following more detailed examples which illustrate, by way of example, the principles of the invention.

Ussing Chamber: Mouse kidney M-1 cells were cultivated in DMEM containing 5% FCS and 5 µM dexamethasone for 10 to 12 days on polyester transwell filters. Filters were inserted into a teflon-coated well-plate which fit into the ussing chamber system. Prior to measurement the medium of M-1 cells was replaced with Caco-2 transport buffer (Invitrogen, Germany). During measurements, the Ussing chamber temperature was kept at 37° C. Short circuit currents (I_sc) were measured in the voltage-clamp mode using an amplifier with the software package Lab View for data acquisition and analysis. The transepithelial electrical resistance (TEER) was determined by the application of voltage steps of ±5 mV every 5 sec. Compounds were administered at a final concentration of 3 µM or at increasing concentrations (e.g. 1-3-10 µM) to the apical solution. At the end of each experiment the amiloride sensitive I_SC was measured by adding 3 µM amiloride to the apical compartment. Results are expressed as inhibition in percent of the amiloride effect or as IC50.

With the example compounds given above, the following IC50 values given in Table 1 were determined in the Ussing Chamber assay:

TABLE 1

| Example | Ussing Chamber IC50 [µM] | Example | Ussing Chamber IC50 [µM] | Example | Ussing Chamber IC50 [µM] |
|---|---|---|---|---|---|
| 1.2 | 0.010 | 1.24 | 0.008 | 7 | 0.010 |
| 1.3 | 0.009 | 1.28 | 0.042 | 1.34 | 0.015 |
| 1.4 | 0.021 | 1.39 | 0.056 | 1.17 | 0.248 |
| 1.15 | 0.011 | 3.1 | 0.025 | 1.16 | 0.002 |
| 1.47 | 0.599 | 1.20 | 0.006 | 1.10 | 0.015 |
| 1.1 | 0.007 | 1.40 | 0.019 | 1.11 | 0.011 |
| 1.6 | 0.004 | 1.41 | 0.022 | 1.9 | 0.015 |
| 1.5 | 0.007 | 1.43 | 0.017 | 2.5 | 0.079 |
| 1.21 | 0.032 | 1.19 | 0.024 | 2.4 | 0.235 |

TABLE 1-continued

| Example | Ussing Chamber IC50 [µM] | Example | Ussing Chamber IC50 [µM] | Example | Ussing Chamber IC50 [µM] |
|---|---|---|---|---|---|
| 1.23 | 0.018 | 1.42 | 0.019 | 1.13 | 0.007 |
| 1.18 | 0.007 | 1.44 | 0.028 | 2.3 | 0.166 |
| 2.8 | 0.035 | 2.7 | 0.036 | 5.1 | 0.010 |
| 1.22 | 0.011 | 1.8 | 0.016 | 2.2 | 0.015 |
| 1.37 | 0.014 | 1.7 | 0.006 | 1.12 | 0.008 |
| 1.38 | 0.012 | 2.6 | 0.291 | 5.2 | 0.046 |
| 1.25 | 0.017 | 1.45 | 0.033 | 6.1 | 0.034 |
| 8 | 0.025 | 1.36 | 0.014 | 4.1 | 0.031 |
| 1.14 | 0.037 | 1.35 | 0.010 | 1.32 | 0.063 |
| 1.26 | 0.013 | 4.2 | 0.007 | 3.3 | 0.044 |
| 1.46 | 0.041 | 5.3 | 0.013 | 1.31 | 0.056 |
| 1.27 | 0.013 | 5.5 | 0.013 | 3.2 | 0.059 |
| 1.30 | 0.030 | 5.4 | 0.039 | 6.2 | 0.006 |
| 1.29 | 0.029 | 3.4 | 0.017 | | |
| 1.33 | 0.010 | 2.1 | 0.304 | | |

COMBINATIONS

The compounds of formula (I) may be used on their own or in conjunction with other active substances of (I) according to the invention. If desired the compounds of formula (I) may also be used in combination with other pharmaceutically active substances. Therefore the invention further relates to medicament combinations which preferably contain, besides one or more compounds of formula (I), as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators, or double or triple combinations thereof.

INDICATIONS

As has been found, the compounds of formula (I) are characterised by their wide range of applications in the therapeutic field. Particular mention should be made of those applications for which the compounds according to the invention of formula (I) are preferably suited on account of their pharmaceutical efficacy as ENaC inhibitors. Examples include respiratory diseases or complaints, or allergic diseases of the airways, Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, pediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Particularly preferably the present invention relates to the use of compounds of formula (I) for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, COPD, chronic bronchitis, chronic sinusitis, asthma, particularly COPD, chronic bronchitis and asthma.

It is most preferable to use the compounds of formula (I) for the treatment of inflammatory and obstructive diseases such as COPD, chronic bronchitis, chronic sinusitis, asthma, cystic fibrosis, particularly COPD, chronic bronchitis and asthma and cystic fibrosis.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

FORMULATIONS

Suitable forms for administration are for example inhalable powders or aerosols. The content of the pharmaceutically effective compound(s) in each case should be in the range from 0.2 to 50 wt %, preferably 5 to 25 wt. % of the total composition, i.e. in amounts which are sufficient to achieve the dosage range specified hereinafter.

Administered by inhalation the active substance combination may be given as a powder, as an aqueous or aqueous-ethanolic solution or using a propellant gas formulation.

Preferably, therefore, pharmaceutical formulations are characterised in that they contain one or more compounds of (I) according to the preferred embodiments above. It is also preferred if the compounds of formula (I) are administered by inhalation, particularly preferably if they are administered once or twice a day. For this purpose, the compounds of formula (I) have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also include concentrates or sterile ready-to-use inhalable solutions. The preparations which may be used according to the invention are described in more detail in the next part of the specification.

Inhalable Powders

If the active substances of formula (I) are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain a compound of formula (I) dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula (I) according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a compound according to the invention and one or more combination partners selected from those described above.

The following example illustrates the present invention without restricting its scope:
Capsule for Powder Inhalation

| 1 capsule contains: | |
|---|---|
| active substance | 0.5 mg |
| lactose for inhalation | 5.0 mg |
| | 5.5 mg |

Preparation:
The active substance is mixed with lactose for inhalation. The mixture is packed into capsules in a capsule-making machine (weight of the empty capsule approx. 50 mg).
weight of capsule: 55.5 mg
size of capsule=3

What we claim:
1. A compound of formula (I),

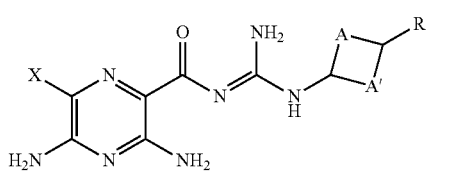

(I)

wherein
A and A' are independently from each other —$CH_2$— or —$CH_2$—$CH_2$—;
R is selected from —$NR^1R^2$, —$NR^3R^4R^{5(+)}Z_1^{(-)}$ and —$OR^{13}$;
X is halogen;
$Z_1^{(-)}$ is a halogen anion or an organic acid anion;
$Z_2^{(-)}$ is a halogen anion or an organic acid anion;
$Z_3^{(-)}$ is a halogen anion or an organic acid anion;
$Z_4^{(-)}$ is a halogen anion or an organic acid anion;
$R^1$ and $R^2$ are selected independently from each other from H, —$C(NH_2)NH$, —$CN(CH_3)_2N(CH_3)_2^+Z_2^-$, —$C_{1-3}$-alkyl, —$C_{2-4}$-alkyl-$N(CH_3)_2$, —$C_{1-3}$-alkyl-phenyl-$R^{12}$, —$C_{1-3}$-alkyl-COOH, —$C_{1-4}$-alkyl-CO—$Y^2$—$R^{11}$, —CO-phenyl-CO—O—$R^{13}$, —CO—$C_{1-4}$-alkyl, —CO—$C_{1-3}$-alkyl-$NR^6R^7$, —CO—$C_{1-3}$-alkyl-$N(CH_3)_3^+Z_3^-$, —CO—$C_{1-4}$-alkyl-$Y^1$—$R^9$,
—CO—O—$C_{1-4}$-alkyl-$R^8$, —CO—NH—$C_{3-7}$-cycloalkyl, —CO—NH—$C_{1-4}$-alkyl, —$CH_2$—CO—O—$C_{1-3}$-alkyl, —$CH_2$—CO—O—$C_{1-3}$-alkyl-phenyl and —$SO_2$—$R^{10}$;
$R^6$ is selected from —$C_{1-3}$-alkyl, H, —$C_{1-4}$-alkyl-OH, —$CH_2$—CO—O—$C_{1-3}$-alkyl and —$CH_2COOH$;
$R^7$ is selected from —$C_{1-3}$-alkyl, —CO—O—$C_{1-3}$-alkyl, —$C_{1-4}$-alkyl-OH, H, —$CH_2$—CO—O—$C_{1-3}$-alkyl and —$CH_2COOH$;
$R^8$ is H or phenyl;
$R^9$ is selected from H, —$C_{1-3}$-alkyl, OH, —$NR^6R^7$ and =O;
$R^{10}$ is $C_{1-3}$-alkyl or an optionally substituted N-containing nonaromatic heterocycle;
$R^{11}$ is selected from H, $C_{1-3}$-alkyl, =O, —$N(CH_3)_2$ and —$N(CH_3)_3^+Z_4^-$;
$R^{12}$ is selected from H, halogen, —COOH, —PO(O$C_{1-4}$-alkyl)OH optionally substituted at the 2,3 or 4 position of the $C_{1-4}$-alkyl group by —$N(C_{1-3}$-alkyl)$_2$ or —$N(C_{1-3}$-alkyl)$_3^+Z_4^-$, and —PO(O$C_{1-4}$-alkyl)$_2$, —PO(OH)$_2$;
$R^{13}$ is H or $C_{1-4}$-alkyl;
$Y^1$ is selected from an optionally substituted 5- to 8-membered N-containing nonaromatic heterocycle, —$N(C_{1-3}$-alkyl)-$C_{2-4}$-alkyl-$N(C_{1-3}$-alkyl)$_2$ and —$N(C_{1-3}$-alkyl)-$C_{2-4}$-alkyl-$N^+(C_{1-3}$alkyl)$_3Z_1^{(-)}$;
$Y^2$ is an optionally substituted 5- to 8-membered N-containing nonaromatic heterocycle;
or $R^1$ and $R^2$ together with the nitrogen atom they are attached to form an optionally substituted 4-7-membered heterocycle selected from the group consisting of piperazino, morpholino, piperidino; thiomorpholino, thiomorpholino-1-oxide, thiomorpholinon-1,1-dioxide, diazepane and pyrrolidino, wherein the nitrogen atoms may be substituted by a group selected from among phenyl, $C_{1-3}$-alkylsulfonyl, $C_{1-3}$-alkyl and —CO—$C_{1-3}$-alkyl;
$R^3$, $R^4$ and $R^5$ denote independently from each other —$C_{1-3}$-alkyl;
or tautomers or pharmacologically acceptable acid addition salts thereof.

2. The compound of formula (I) according to claim 1, wherein
A and A' are both —$CH_2$—$CH_2$—;
R is —$NR^1R^2$ or —$NR^3R^4R^{5(+)}X^{(-)}$;
X is halogen;
$R^1$ and $R^2$ are selected independently from each other from H, —$C(NH_2)NH$, —$CN(CH_3)_2N(CH_3)_2^+Z_2^-$, —$C_{1-3}$-alkyl, —$C_{2-4}$-alkyl-$N(CH_3)_2$—$C_{1-3}$-alkyl-phenyl-$R^{12}$, —$C_{1-3}$-alkyl-COOH, —$C_{1-4}$-alkyl-CO—$Y^2$—$R^{11}$, —CO-phenyl-CO—O—$R^{13}$, —CO—$C_{1-4}$-alkyl, —CO—$C_{1-3}$-alkyl-$NR^6R^7$, —CO—$C_{1-3}$-alkyl-$N(CH_3)_3^+$
$Z_3^-$, —CO—$C_{1-4}$-alkyl-$Y^1$—$R^9$, —CO—O—$C_{1-4}$-alkyl-$R^8$, —CO—NH—$C_{3-7}$-cycloalkyl, —CO—NH—$C_{1-4}$-alkyl, —$CH_2$—CO—O—$C_{1-3}$-alkyl, —$CH_2$—CO—O—$C_{1-3}$-alkyl-phenyl, —$SO_2$—$R^{10}$;
$R^6$ is selected from —$C_{1-3}$-alkyl, H, —$C_{1-4}$-alkyl-OH, —$CH_2$—CO—O—$C_{1-3}$-alkyl and —$CH_2COOH$;
$R^7$ is selected from —$C_{1-3}$-alkyl, —CO—O—$C_{1-3}$-alkyl, —$C_{1-4}$-alkyl-OH, H, —$CH_2$—CO—O—$C_{1-3}$-alkyl and —$CH_2COOH$;
$R^8$ is H or phenyl;
$R^9$ is selected from H, —$C_{1-3}$-alkyl, —OH, —$NR^6R^7$ and =O;
$R^{10}$ is $C_{1-3}$-alkyl or an optionally substituted N-containing nonaromatic heterocycle;

R$^{11}$ is selected from H, —C$_{1-3}$-alkyl, =O, —N(CH$_3$)$_2$ and —N(CH$_3$)$_3$$^+$X$^-$;

R$^{12}$ is H or halogen;

R$^{13}$ is H or —C$_{1-4}$-alkyl;

Y$^1$ is an optionally substituted 5- to 8-membered N-containing nonaromatic heterocycle, Y$^2$ is an optionally substituted 5- to 8-membered N-containing nonaromatic heterocycle, or R$^1$ and R$^2$ together with the nitrogen atom they are attached to form an optionally substituted 4-7-membered heterocycle selected from the group consisting of piperazino, morpholino, piperidino; thiomorpholino, thiomorpholino-1-oxide, thiomorpholinon-1,1-dioxide, diazepane and pyrrolidino, wherein the nitrogen atoms may be substituted by a group selected from among phenyl, C$_{1-3}$-alkylsulfonyl, C$_{1-3}$-alkyl and —CO—C$_{1-3}$-alkyl;

R$^3$, R$^4$ and R$^5$ are selected independently from each other —C$_{1-3}$-alkyl;

or tautomers or pharmacologically acceptable acid addition salts thereof.

3. The compound of formula (I) according to claim 1, wherein

R is —NR$^1$R$^2$;

or tautomers or pharmacologically acceptable acid addition salts thereof.

4. The compound of formula (I) according to claim 1, wherein

R$^1$ and R$^2$ are independently from each other H, —C$_{1-4}$-alkyl-CO—Y$^2$—R$^{11}$ or —CO—C$_{1-4}$-alkyl-Y$^1$—R$^9$;

R$^9$ is selected from H, —C$_{1-3}$-alkyl, —OH, —NR$^6$R$^7$ and =O;

R$^{11}$ is selected from H, —C$_{1-3}$-alkyl, =O, —N(CH$_3$)$_2$ and —N(CH$_3$)$_3$$^+$X$^-$;

Y$^1$ is selected from a linker of formula (a1) to (j1)

(a1)

(b1)

(c1)

(d1)

(e1)

(f1) 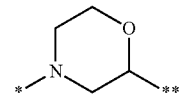

(g1) 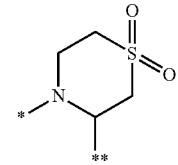

(h1) 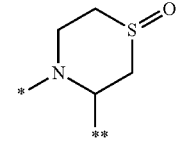

(i1) 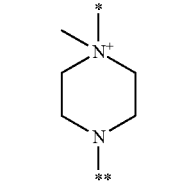

(j1) 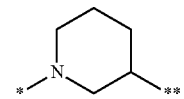

wherein

* denotes the attachment point to the alkyl moiety of —CO—C$_{1-4}$-alkyl-*

** denotes the attachment point to R$^9$;

Y$^2$ is selected from a linker of formula (a2) to (h2)

(a2) 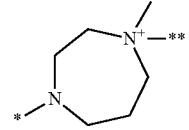

(b2) 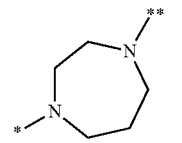

(c2) 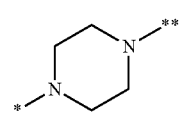

(d2) 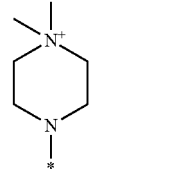

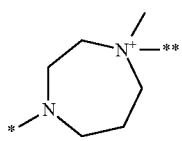
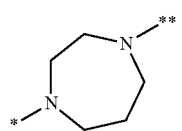
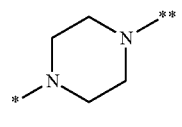
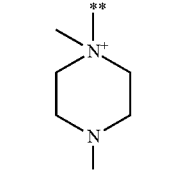
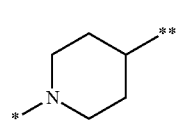

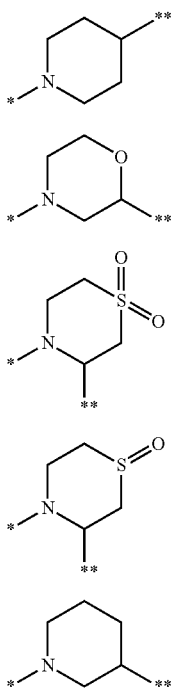

wherein
*denotes the attachment point to the carbonyl moiety of —$C_{1-4}$-alkyl-CO—*
**denotes the attachment point to $R^{11}$;
or tautomers or pharmacologically acceptable acid addition salts thereof.

5. The compound of formula (I) according to claim 1, wherein
$R^1$ and $R^2$ independently from each other denote H, —$C(NH_2)NH$ or —$CN(CH_3)_2N(CH_3)_2{}^+Z_2{}^-$;
or tautomers or pharmacologically acceptable acid addition salts thereof.

6. The compound of formula (I) according to claim 1, wherein
$R^1$ and $R^2$ independently from each other are selected from —$C_{1-3}$-alkyl, —$C_{2-4}$-alkyl-$N(CH_3)_2$, —$C_{1-3}$-alkyl-phenyl-$R^{12}$, —$C_{1-3}$-alkyl-COOH, —$CH_2$—CO—O—$C_{1-3}$-alkyl and —$CH_2$—CO—O—$C_{1-3}$-alkyl-phenyl;
or tautomers or pharmacologically acceptable acid addition salts thereof.

7. The compound of formula (I) according to claim 1, wherein
$R^1$ and $R^2$ independently from each other are selected from CO-phenyl-CO—O—$R^{13}$, —CO—$C_{1-4}$-alkyl and —CO—$C_{1-3}$-alkyl-$NR^6R^7$;
or tautomers or pharmacologically acceptable acid addition salts thereof.

8. The compound of formula (I) according to claim 1, wherein
$R^1$ and $R^2$ independently from each other are selected from —CO—O—$C_{1-4}$-alkyl-$R^8$ and —$SO_2$—$R^{10}$;
or tautomers or pharmacologically acceptable acid addition salts thereof.

9. The compound of formula (I) according to claim 1, wherein
$R^1$ and $R^2$ are hydrogen;
or tautomers or pharmacologically acceptable acid addition salts thereof.

10. A pharmaceutical composition comprising a compound according to claim 1 or a pharmaceutically acceptable salt thereof and a pharmaceutically acceptable carrier.

\* \* \* \* \*